(12) United States Patent
Mathiesen et al.

(10) Patent No.: US 6,958,060 B2
(45) Date of Patent: Oct. 25, 2005

(54) METHOD FOR MUSCLE DELIVERY OF DRUGS, NUCLEIC ACIDS AND OTHER COMPOUNDS

(75) Inventors: Iacob Mathiesen, Oslo (NO); Terje Lomo, Oslo (NO)

(73) Assignee: Genetronics, Inc., San Diego, CA (US)

( * ) Notice: Subject to any disclaimer, the term of this patent is extended or adjusted under 35 U.S.C. 154(b) by 20 days.

(21) Appl. No.: 10/620,271

(22) Filed: Jul. 14, 2003

(65) Prior Publication Data

US 2004/0092907 A1 May 13, 2004

Related U.S. Application Data

(63) Continuation of application No. 10/141,561, filed on May 7, 2002, now Pat. No. 6,610,044, which is a continuation of application No. 09/899,561, filed on Jul. 5, 2001, now abandoned, which is a continuation of application No. 09/565,140, filed on May 5, 2000, now Pat. No. 6,261,281, which is a continuation-in-part of application No. 09/055,084, filed on Apr. 3, 1998, now Pat. No. 6,110,161.

(60) Provisional application No. 60/042,594, filed on Apr. 3, 1997.

(51) Int. Cl.[7] ............................................. A61M 31/00
(52) U.S. Cl. ........................ 604/511; 604/522; 604/21
(58) Field of Search ............................. 604/20–21, 500, 604/522, 511; 435/173.6, 285.2

(56) References Cited

U.S. PATENT DOCUMENTS

| | | |
|---|---|---|
| 5,273,525 A | 12/1993 | Hofmann |
| 5,304,120 A | 4/1994 | Crandell et al. |
| 5,318,514 A | 6/1994 | Hofmann |
| 5,389,069 A | 2/1995 | Weaver |
| 5,468,223 A | 11/1995 | Mir |

(Continued)

FOREIGN PATENT DOCUMENTS

| | | |
|---|---|---|
| WO | WO 95/23211 | 8/1995 |
| WO | WO 98/27966 | 7/1998 |
| WO | WO 98/43702 | 10/1998 |
| WO | WO 99/21175 | 1/1999 |
| WO | WO 00/45823 | 8/2000 |

OTHER PUBLICATIONS

Alhara, et al., "Gene Transfer into Muscle by Electroporation In Vivo", *Nature Biotechnology*, (1998), 867–870, vol. 16.

Bachy, Monique, et al: "Electric Pulses Increase The Immunogenicity Of An Influenza DNA Vaccine Injected Intramuscularly In The Mouse" *Vaccine*, (2001), 1688–1693, 19: 13–14, Elsevier Science Ltd, www.elsevier.com/locate/vaccine.

Bhatt, D.; et al.; "Rhabdomyolysis Due to Pulsed Electric Fields" *Plastics and Reconstructive Surgery*, (1990), 1–11, 86:1.

(Continued)

*Primary Examiner*—Mark Bockelman
(74) *Attorney, Agent, or Firm*—Daniel M. Chambers; Douglas C. Murdock; BioTechnology Law Group

(57) ABSTRACT

A method is disclosed for delivering molecules such as pharmaceutical drugs and nucleic acids into skeletal muscle in vivo. The molecule is first injected into the muscle at one or multiple sites. Immediately or shortly after injection, electrodes are placed flanking the injection site and a specific amount of electrical current is passed through the muscle. The electrical current makes the muscle permeable, thus allowing the molecule to enter the cell. In the case where nucleic acid is injected, the efficiency of transfer permits expression of protein encoded by the nucleic acid in an amount that exhibits systemic biological activity and which generates a robust immune response.

34 Claims, 31 Drawing Sheets

U.S. PATENT DOCUMENTS

| | | | |
|---|---|---|---|
| 5,501,662 A | 3/1996 | Hofmann | |
| 5,674,267 A | 10/1997 | Mir et al. | |
| 5,702,359 A | 12/1997 | Hofmann et al. | |
| 5,810,762 A | 9/1998 | Hofmann | |
| 5,944,710 A | 8/1999 | Dev et al. | |
| 5,964,726 A | 10/1999 | Korenstein et al. | |
| 5,993,434 A | 11/1999 | Dev et al. | |
| 6,009,347 A | 12/1999 | Hofmann | |
| 6,041,252 A | 3/2000 | Walker et al. | |
| 6,261,281 B1 * | 7/2001 | Mathiesen et al. | 604/500 |
| 6,610,044 B2 * | 8/2003 | Mathiesen | 604/522 |
| 2003/0018006 A1 | 1/2003 | Tao et al. | |

OTHER PUBLICATIONS

Block, T.A., et al., "Nonthermally Mediated Muscle Injury and Necrosis in Electrical Trauma", *Journal of Burn Care & Rehabilitation*, (1995), 581–588, 16:6.

Collas, P., et al., "The Nuclear Localization Sequence of the SV40 T Antigen Promotes Transgene Uptake and Expression in Zebrafish Embryo Nuclei", *Transgenic Research*, (1996), 451–458, vol. 5.

Danko, I., et al, "Pharmacological Enhancement Of in Vivo Foreign Gene Expression In Muscle" *Gene Therapy*, (1994) 114–121, 1:2, Macmillan Press Ltd., BASINGSTOKE, GB, Mar. 1994.

Davis, H.L., et al., "Direct Gene Transfer into Skeletal Muscle In Vivo: Factors Affecting Efficiency of Transfer and Stability of Expression", *Human Gene Therapy*, (1993), 151–159, vol. 4.

Heller, R., et al., "In Vivo Gene Electroinjection and Expression in Rat Liver" (1996), FEBS Letter, 225–228, vol. 389.

Hiroyuki, A., et al., "Gene Transfer into Muscle by Electroporation In Vivo", *Nature Biotechnology*, (1998), 867–870, vol. 16.

Hoffman, G.A., "Cell in Electric Fields", *In Electroporation and Electrofusion in Cell Biology, ed.,* Neuman, E.; Sowers, A.E. & Jordan, C.A., (1989), 3849–407, Plenum Publishing Corporation.

Katsumi, et al., "Humoral and Cellular Immunity to an Encoded Protein Induced by Direct DNA Injection", *Human Gene Therapy*, (1994), 1335–1339, vol. 5.

Kadowaki, Shin–Etsu, et al: "Protection Against Influenza Virus Infection in Mice Immunized By Administration Of Hemagglutinin–Expressing DNAs With Electroporation" *Vaccine*, (2000), 2779–2788, vol. 18, Elsevier Science Ltd., www.elsevier.com/locate/vaccine.

Le Borgne, Sylvie, et al., "In Vivo Induction Of Specific Cytotoxic T Lymphocytes In Mice And Rhesus Macaques Immunized With DNA Vector Encoding An HIV Epitope Fused With Hepatitis B Surface Antigen." *Virology*, (1998), 304–315, 240:2, Article No.: VY978942, Academic Press.

Lee, R.C., et al., "Transient and Stable Ionic Premeabilization of Isolated Skeletal Muscle Cells After Electrical Shock", *Journal of Burn Care & Rehabilitation*, (1993), 528–540, 14:5.

Lim, et al., "Potentiation of Antigen–Specific, Th1 Immune Responses by Multiple DNA Vaccination with an Ovalbumin/Interferon-$_{13}$ Hybrid Construct", *Immunology*, (1998), 135–141, vol. 94.

Manthorpe, M., et al., "Gene Therapy by Intramuscular Injection of Plasmid DNA: Studies on Firefly Luciferase Gene Expression in Mice", *Human Gene Therapy*, (1993), 419–431, vol. 4.

Martinez, et al., "Combining DNA and Protein Vaccines for Early Life Immunization Against Respiratory Syncytial Virus in Mice", *European Journal of Immunology*, (1999), 3390–3400, 29:10 Abstract.

Marthiesen, I.: "Electropermeabilization Of Skeletal Muscle Enhances Gene Transfer In Vivo." *Gene Therapy*, (1999), 508–514, 6:4, Stockton Press, www.stockton.press.co.uk/gt.

Mendiratta, Sanjeev Kumar, et al: "Therapeutics tumor immunity induced by polyimmunization with melanoma antigens gp100 and TRP–2" *Cancer Research*, (2001) 859–863, 61:3.

Miklavcic, D., et al., "The Importance of Electric Field Distribution for Effective In Vivo Electroporation of Tissues", *Biophysical Journal*, (1998), 2152–2158, vol. 74.

Nishi, T., et al., "High–Efficiency in Vivo Gene Transfer Using Intraarterial Plasmid DNA Injection Following In Vivo Electroporation", *Cancer Research*, (1996), 1050–1055, vol. 56.

Pelegrin, et al., "Genetically Engineered Antibodies In Gene Transfer and Gene Therapy", *Human Gene Therapy*, (1998), 2165–2175, vol. 9.

Potter, H., "Electroporation in Biology: Methods, Applications, and Instrumentation", [Review], *Analytical Biochemistry*, (1998), 361–373, vol. 174.

Prausnitz, M.R., et al., "Electroporation of Mammalian Skin: A Mechanism of Enhance Transdermal Drug Delivery", *Proc. Natl. Acad. Sci. USA*, (1993), 10504–10508, vol. 90.

Richmond, et al., "Studies of the Neutralizing Activity and Avidity of Anti–Human Immunodeficiency Virus Type 1 Env Antibody Elicited by DNA Priming and Protein Boosting", *Journal of Virology*, (1998), 9092–9100, 72:11 Abstract.

Rols, M.P., et al., "Electropermeabilization of Mammalian Cells: Quantitative Analysis of the Phenomenon", *Biophysical Journal*, (1990), 1089–1098, vol. 58.

Rols, M.P., et al., "In Vivo Electrically Mediated Protein and Gene Transfer in Murine Melanoma", *Nature Biotechnology*, (1998), 168–171, vol. 16.

Selby, Mark, et al., "Enhancement of DNA vaccine potency by electroporation in vivo," *Journal Of Biotechnology*, (2000), 147–152, 83:1–2, Elsevier Science B.V., www.elsevier.com/locate/biotec.

SIN, Jeong–Im, et al., "DNA priming–protein boosting enhances both antigen–specific antibody and Th1–type cellular Immune reponses in a murine herpes simplex virus–2 gD vaccine model", *DNA And Cell Biology*, (1999), 771–779, 18:10.

Smith, L.C., et al., "Advances In Plasmid Gene Delivery And Expression In Skeletal Muscle", *Curr. Opin. Mol. Ther.*, (2000), 150–154, vol. 39.

Tekle, E., et al., "Electroporation by Using Bipolar Oscillating Electric Field: An Improved Method for DNA Transfection of NIH 3T3 Cells", *Pro. Natl. Acad. Sci. USA*, (1991), 4230–4234, vol. 88.

"The Effects of a Single High Voltage Electrical Stimulation with an Anticancer Drug in In Vivo Growing Malignant Tumors", *Japanese Journal of Surgery*, (1990), 197–204, 20:2.

Widera, G., et al., "Increased DNA Vaccine Delivery and Immunogenecity by Electroporation In Vivo", *The Journal of Immunology*, (2000), 4635–4640, vol. 164.

Wolf, H., et al., "Control by Pulse Parameters of Electric Field–Mediated Gene Transfer in Mammalian Cells", *Biophysical Journal*(1994), 524–531, vol. 66.

Wolff, J.A., et al., "Long–Term Persistence of Plasmid DNA and foreign Gene Expression in Mouse Muscle", *Human Molecular Genetics*, (1992), 363–369, 1:6.

Wolff, J.A. et al., "Conditions Affecting Direct Gene Transfer into Rodent Muscle In Vivo", *Biotechniques*, (1991), 474–485, 11:4, XP000973460.

Zewert, Thomas E., et al., "Creation of Transdermal Pathways for Micromolecule Transport by Skin Electroporation and a Low Toxicity, Pathway Enlarging Molecule", Bioelectrochemistry and Bioenergetics, (1999), 11–20, 49:1, Elsevier Science S.A., www.elsevier.com/locate/biochem.

Zhu et al., "DNA fusion vaccines against B–cell tumors," Trends Mol Med 7:566–572 (2001).

Zucchelli, S., et al., "Enhancing B–and T–Cell Immune Response to a Hepatitis C Virus E2 DNA Vaccine by Intramuscular Electrical Gene Transfer". *Journal of Virology*, (2000), 11598–11607, 74:24, American Society for Microbiology.

* cited by examiner

EDL, fast   SOL, slow a) *All muscles are denervated*

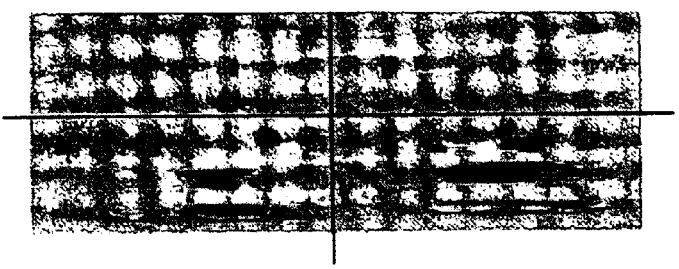

Not stimulated

Stimulated, 100 Hz after DNA injection b) *All muscles are stimulated directly with 100 Hz after DNA injection*

Innervated

Denervated c) *All muscles have been active*

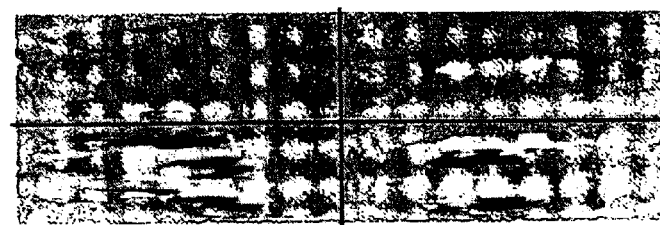

Nerve stimulation after DNA injection

Direct muscle stimulation after DNA injection d) *All muscles have been stimulated directly with 100 Hz*

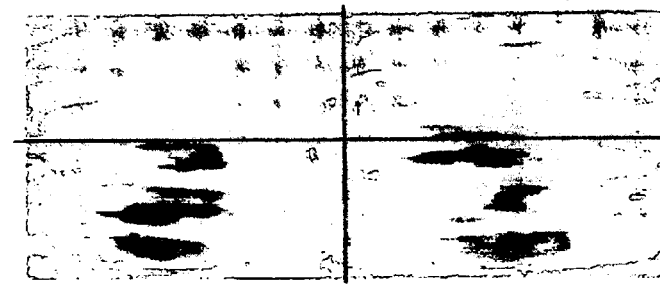

Stimulated 10 min. prior to DNA injection

Stimulated immediately after DNA injection

Fig. 3

METHOD FOR MUSCLE DELIVERY OF DRUGS, NUCLEIC ACIDS AND OTHER COMPOUNDS

CROSS-REFERENCE TO RELATED PATENT APPLICATIONS

This application is a continuation of U.S. patent application Ser. No. 10/141,561 filed May 7, 2002, now U.S. Pat. No. 6,610,044 and entitled "Method for Genetic Immunization" which is a continuation of U.S. patent application Ser. No. 09/899,561 filed Jul. 5, 2001, now abandoned and entitled "Method for Genetic Immunization and Introduction of Molecules into Skeletal Muscle and Immune Cells," which is a continuation of U.S. application Ser. No. 09/565,140 (now U.S. Pat. No. 6,261,281), filed May 5, 2000 and entitled "Method for Genetic Immunization and Introduction of Molecules into Skeletal Muscle and Immune Cells", which is a continuation-in-part of U.S. patent application Ser. No. 09/055,084 (now U.S. Pat. No. 6,110,161), filed Apr. 3, 1998, and entitled "Method for Introducing Pharmaceutical Drugs and Nucleic Acids Into Skeletal Muscle," which is related to and claims the benefit of U.S. Provisional Application Ser. No. 60/042,594, filed Apr. 3, 1997, and entitled "Apparatus and Method for Introducing Pharmaceutical Drugs and Genetic Material Into Skeletal Muscle." These applications are hereby incorporated by reference.

BACKGROUND OF THE INVENTION

1. Field of the Invention

The present invention is related to a method for making skeletal muscle semipermeable to pharmaceutical drugs, nucleic acids and other molecules. More specifically, skeletal muscle is made semipermeable by electrically stimulating the muscle with a current that generates low field strengths following injection of pharmaceutical drugs, nucleic acids and other molecules. The method can be used to obtain expression of proteins encoded by nucleic acids administered to muscle in accordance with the method.

2. Technical Background

Scientists are continually discovering genes which are responsible for many human diseases, such as genes responsible for some forms of breast cancer, colon cancer, muscular dystrophy and cystic fibrosis, In addition, scientists are continually discovering genes that code for bacterial and viral antigens (e.g., viral capsid proteins). Despite these new discoveries, a major obstacle facing the medical profession is how to safely deliver effective quantities of these agents to patients to treat disease or for genetic immunization.

Currently, most pharmaceutical agents are taken orally or intravenously. Oral and intravenous drug and gene delivery methods, however, have several shortcomings. First, a large percent of orally or intravenously delivered drugs are degraded by the body before arriving at the target organ or cells. Acids and enzymes in the stomach and intestine, for example, can break down many pharmaceutical drugs. Similarly, genes would be rapidly destroyed by proteins found in the blood and liver which break down DNA. Additionally, intravenously delivered drugs and genes are often sequestered by the liver or immune system before arriving at the diseased organ or cells. Second, oral and intravenous drug and gene delivery is non-specific. That is, the drug or gene is delivered to both target and non-target cells.

Skeletal muscle is a promising candidate for drug delivery, gene therapy and genetic immunization. First, skeletal muscle constitutes over 50% of a human's body mass, most of which is easily accessible compared to other tissues and organs of the body. Second, there are numerous inherited and acquired disorders, such as Duchenne muscular dystrophy (DMD), diabetes mellitus, hyperlipidaemia and cardiovascular disease which are good candidate disorders for drug and gene delivery into the muscle. Third, muscle is an ideal site for genetic immunization because it is easily accessible and proteins made in the muscle are secreted, thus eliciting an immune response. Finally, skeletal muscle cells are non-dividing. Therefore, skeletal muscle cells are capable of expressing a protein coded by a gene for a longer time period than would be expected of other cell types that are continually dividing. Because the protein is expressed for a longer time, fewer treatments would be necessary.

Currently, however, there is no non-viral method for effectively delivering pharmaceutical drugs, proteins, and DNA into skeletal muscle in vivo. There are several methods known in the art for transferring pharmaceutical drugs and DNA into skeletal muscle, such as intramuscular injection of DNA. The clinical applicability of direct muscle injection, however, is limited mainly because of low transfection efficiency, typically less than 1% transfection efficiency. It has been demonstrated that the efficacy of transfection can be improved if DNA injections are done in regenerating muscle. Regeneration is induced three days before DNA injection with the drug Bivucain. While injection in regenerating muscles induced by Bivucain show higher efficiency, the method has limited applicability in humans because of the severe damage caused to the muscle.

From the foregoing, it will be appreciated that it would be an advancement in the art to provide a non-viral method of delivering pharmaceutical drugs and DNA only to diseased organs and cells. It would also be an advancement in the art to provide an electroporation method of delivering pharmaceutical drugs and DNA directly into skeletal muscle. It would be yet another advancement in the art if the electroporation method could deliver therapeutically effective quantities of pharmaceutical drugs and DNA into the skeletal muscle at multiple sites simultaneously. It would be a further advancement if the method permitted the delivery efficiencies to be regulated.

Such a method is disclosed herein.

SUMMARY OF THE INVENTION

The present invention provides a method for delivering or transfecting pharmaceutical drugs, proteins, and DNA into skeletal muscle and other cells residing within the skeletal muscle. Without being bound by theory, the method is thought to be similar to electroporation. Electroporation works on the principle that a cell acts as an electrical capacitor and is generally unable to pass current. Subjecting cells to a high-voltage electric field, therefore, creates transient permeable structures or micropores in the cell membrane. These pores are large enough to allow pharmaceutical drugs, DNA, and other polar compounds to gain access to the interior of the cell. With time, the pores in the cell membrane close and the cell once again becomes impermeable.

Conventional electroporation, however, employs high field strengths from 0.4 to several kV/cm. In contrast to conventional electroporation, the field strength used in the present invention ranges from about 10 V/cm to about 300 V/cm. These lower field strengths are thought to cause less muscle damage without sacrificing, and indeed increasing, transfection efficiencies. Furthermore, using the method of the present invention, transfection efficiencies can be tightly regulated by altering such parameters as frequency, pulse duration and pulse number.

The increase in DNA transfection efficiency is observed only if the muscle is electrically stimulated immediately, or shortly after the DNA injection. Thus, the semipermeable quality of the tissue induced by the stimulation is reversible. Moreover, it is dependent on current through the muscle; activity induced through the nerve does not affect transfection efficiency.

Once transfected, the muscle cells are able to express the proteins coded by the nucleic acid. Therefore, the transfection method of the present invention can be used, for example, to transfect expression vectors for genetic immunization (i.e., DNA vaccines). In one embodiment, rabbits were transfected with a plasmid containing the cDNA for rat agrin. The transfected muscles produced and secreted agrin protein. Nineteen days post-transfection, rabbit serum contained significant antibodies against rat agrin.

In a second embodiment, mice and rats were transfected using the method of the present invention with one or more of three different eukaryotic expression vectors containing the coding sequences for DH-CNTF, an agonistic variant of human ciliary neurotrophic factor, AADH-CNTF, an antagonistic variant of human ciliary neurotrophic factor and sec-DHCNTF, a secreted form of DH-CNTF. The muscles were either not electrically stimulated or stimulated immediately after DNA injection. Blood was collected at various time points and the antibody titers determined. In both rats and mice, electrical stimulation immediately after DNA injection led to approximately 5 to 10-fold higher antibody titers than simple DNA injection.

The transfection method of the present invention can also be used to systemically deliver proteins to treat diseases. In one preferred embodiment, a DNA plasmid harboring the erythropoietin (EPO) gene was injected into skeletal muscle and stimulated according to the method of the present invention. Controls were either not stimulated or transfected with a control vector not harboring the EPO gene. After 14 days, only the mice transfected with EPO according to the method of the present invention displayed an increased hematocrit indicating the transfected muscles were able to produce and secrete into the blood stream substantial amounts of EPO.

Non-nucleic acids may also be transfected by the method of the present invention. In one embodiment, rhodamin conjugated dextran was injected into the muscle followed by electrical stimulation. Three to five days later the muscles were frozen in liquid nitrogen and sectioned on a cryostat. Fluorescence was observed in cells injected and stimulated, indicating the rhodamin conjugated dextran was able to enter and remain in the muscle cells.

In order to reduce pain that may be associated with the method of the present invention, a local anesthetic can be injected at the site of treatment prior to or in conjunction with the injection of DNA. For example, in one embodiment of the current invention, DNA may be mixed with Marcain, a local anesthetic, followed by electroporation.

These and other objects and advantages of the present invention will become apparent upon reference to the accompanying drawings and graphs and upon reading the following detailed description and appended claims.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

A more particular description of the invention briefly described above will be rendered by reference to the appended drawings and graphs. These drawings and graphs only provide information concerning typical embodiments of the invention and are not therefore to be considered limiting of its scope.

FIG. 3—illustrates whole mounts of muscles which have been injected with 50 $\mu$l of RSV-Lac Z Plasmid DNA solution at a concentration of 1 $\mu$g/$\mu$l. Muscles in 3a and 3b were taken out 15 days after DNA injection. Muscles in 3c and 3d were taken out 7 days after DNA injection. All muscles are pairs from the same rat.

FIG. 13—is a graph illustrating the voltage dependency of the stimulation method of the present invention.

FIG. 17—is a photograph of transfected muscles illustrating damage caused by stimulation and regeneration of the muscle after a short period of time.

DETAILED DESCRIPTION OF THE PREFERRED EMBODIMENTS

The present invention is directed to a novel method for increasing the permeability of skeletal muscle tissue and other cells residing therein, thus allowing pharmaceutical drugs, proteins, and nucleic acids to enter or transfect the cells. The method of the present invention passes a predetermined amount of electrical current through the skeletal muscle tissue. Unlike previously described electroporation methods, however, the parameters of the method of the present invention are unique, particularly with respect to the low field strength used and the amount of damage that occurs. Other parameters such as the number of trains, frequency, pulse number and pulse duration can be varied in order to regulate the amount of pharmaceutical drug, protein, or nucleic acid delivered.

Figure 1:
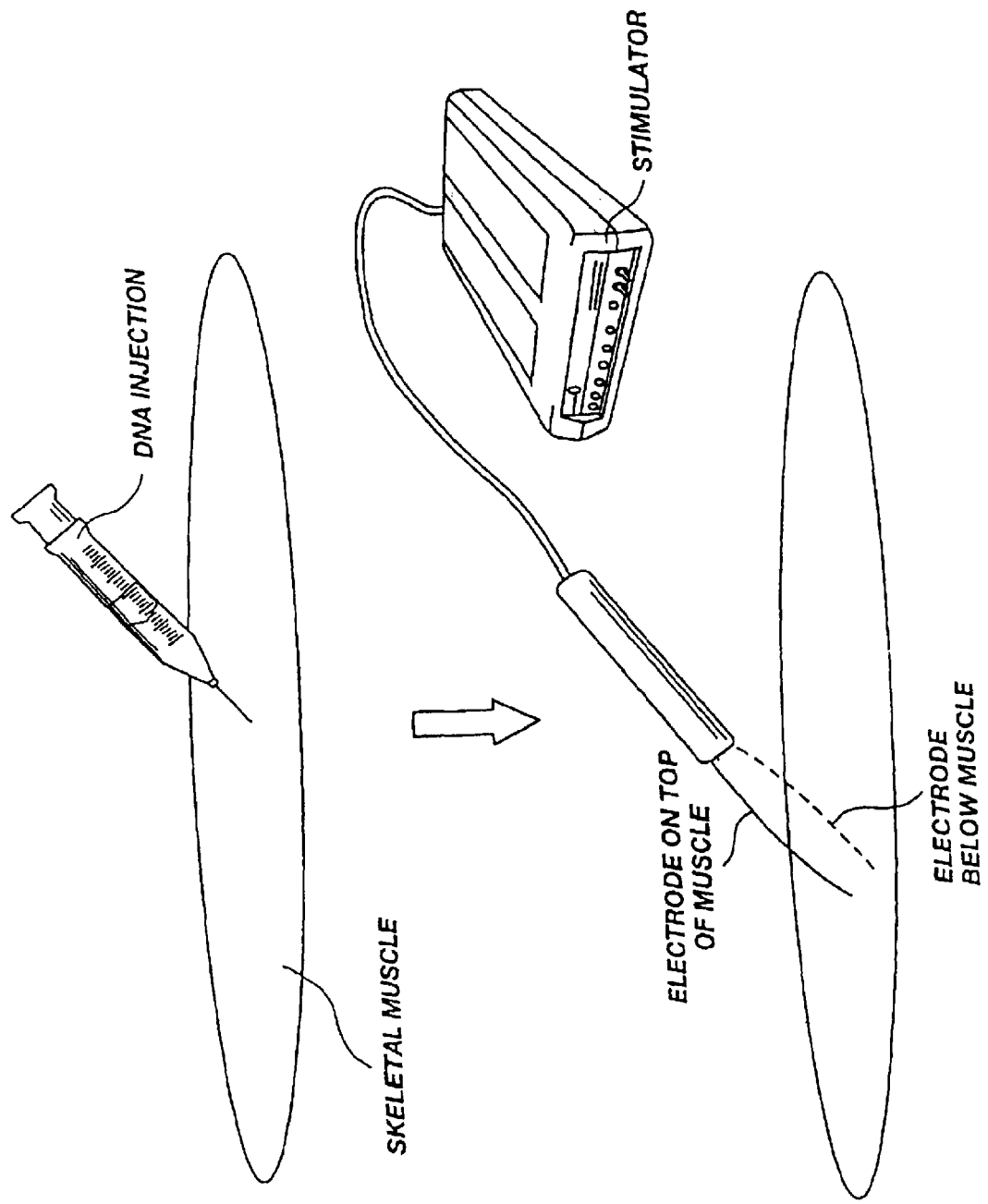
FIG. 1—graphically illustrates the method of delivering pharmaceutical drugs and DNA into skeletal muscle of the present invention.

As illustrated in FIG. 1, generally, skeletal muscle is exposed and a predetermined amount of a molecule is injected into the muscle. In one embodiment the DNA is dissolved in 0.9% sodium chloride (NaCl). The exact solvent, however, is not critical to the invention. For example, it is well known in the art that other solvents such as sucrose are capable of increasing DNA uptake in skeletal muscle. Other substances may also be co-transfected with the molecule of interest for a variety of beneficial reasons. For example, P188 (Lee, et al. PNAS., 4524–8, 10, 89 (1992)), which is known to seal electropermeabilized membranes, may beneficially affect transfection efficiencies by increasing the survival rate of transfected fibers.

With continued reference to FIG. 1, electrodes are placed on the muscle, about 1–4 mm apart, near the area where the molecule was injected. The exact position or design of the electrodes is not critical so long as current is permitted to pass through the muscle fibers perpendicular to their direction in the area of the injected molecule.

Figure 2:
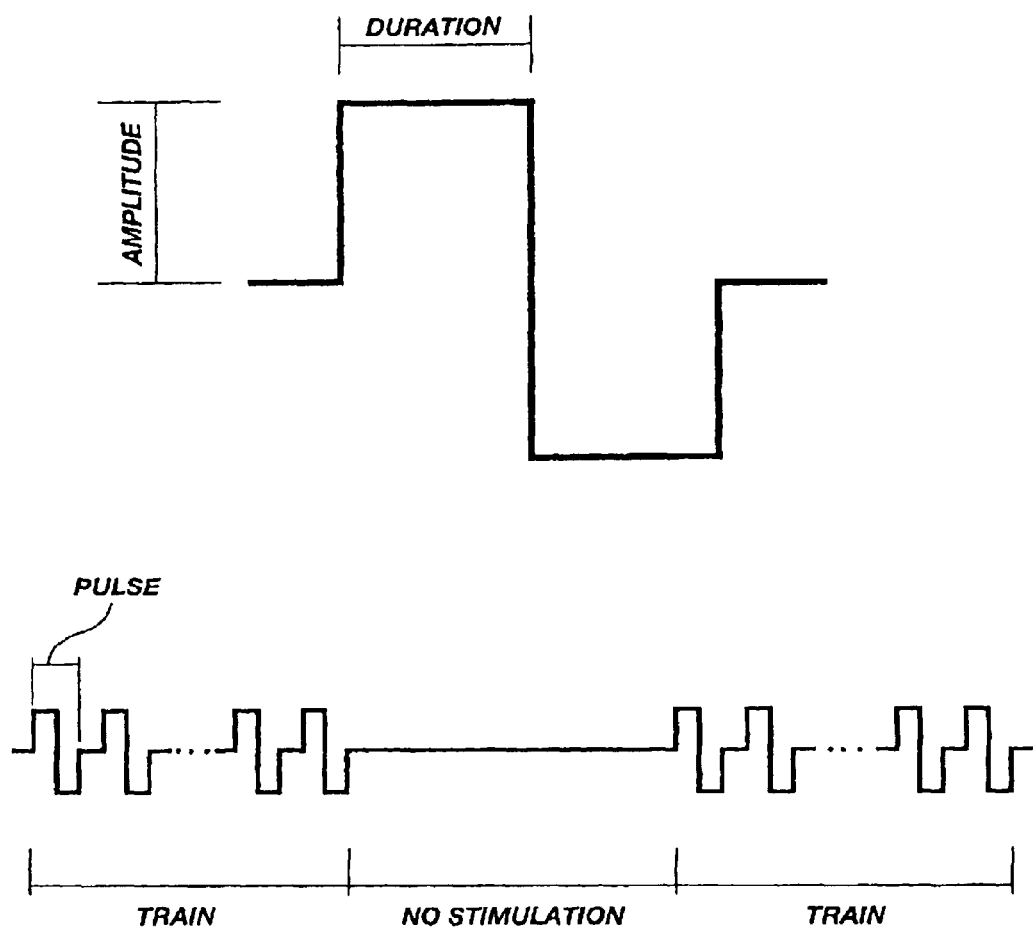
FIG. 2—is a graphical illustration of an electrical stimulation delivered according to the method of the present invention.

Once the electrodes are in position, the muscle is electroporated or stimulated. As illustrated in FIG. 2, the stimulation is delivered as a square bipolar pulse having a predetermined amplitude and duration. In order to optimize the transfection efficiencies, these parameters have been widely varied and transfection efficiencies compared. For example, the voltages have ranged from approximately 0 to 50 volts; the pulse durations have ranged from 5 $\mu$s to 5 ms; the number of pulses have ranged from a single pulse to 30,000 pulses; and the pulse frequency within trains have ranged from 0.5 Hz to 1000 Hz.

The conclusion from these results is that so long as the field strength is above about 50 V/cm, the other parameters may be varied depending on the experimental conditions desired. While no upper limit was detected, effective transfection efficiencies were observed with much higher field strengths. The field strength of the stimulation can be calculated using the formula:

$$E=V/(2r\ln(D/r)),$$

which gives the electric field between wires if D>>r. In the formula, V=voltage=10 V, D=distance between wire centers 0.1–0.4 cm, r=diameter of electrode=0.06 cm. See Hofmann, G. A. Cells in electric fields. In E. Neumann, A. E. Sowers, & C. A. Jordan (Eds.), Electroporation and electrofusion in cell biology (pp. 389–407). Plenum Publishing Corporation (1989). At 10 volts, the field strength is between 163 V/cm–43 V/cm (from 0.1 to 0.4 cm between electrodes, respectively). Because D is not much greater than r, it may be more appropriate to use the formula for electric fields between large parallel plates:

$$E=V/D$$

This gives a similar field strength of between 100 V/cm–25 V/cm (from 0.1–0.4 cm between electrodes, respectively). It will be appreciated that the field strength, as well as other parameters, are affected by the tissue being transfected, and thus optimal conditions may vary. Using the parameters given in the present invention, however, optimal parameters can be easily obtained by one skilled in the art.

As illustrated in FIGS. 3 and 5–8, the method of the present invention dramatically increases the efficiency of drug and DNA delivery into skeletal muscle. In one embodiment, rat soleus or EDL muscles were injected with DNA plasmid containing the β-galactosidase gene (lac Z). The β-galactosidase gene yields a protein capable of converting a colorless substrate into a blue substrate that can be visually analyzed or measured spectrophotometrically. FIG. 3 depicts representative soleus and EDL muscles that have been transfected with β-galactosidase gene using various stimulation parameters.

FIG. 3a illustrates the improved DNA delivery efficiency of soleus and EDL muscles that have been transfected according to the method of the present invention. Soleus and EDL muscles (n=3) were first denervated by transecting the sciatic nerve. This was done to eliminate any influence of nerve-induced activity that arguably could contribute to the increased transfection efficiency observed. Three days post-denervation, the muscles were injected with the β-galactosidase gene as described above. After the DNA injection, the muscles were either untreated or, immediately after the DNA injection, the muscles were stimulated according to the method of the present invention.

Figure 4:
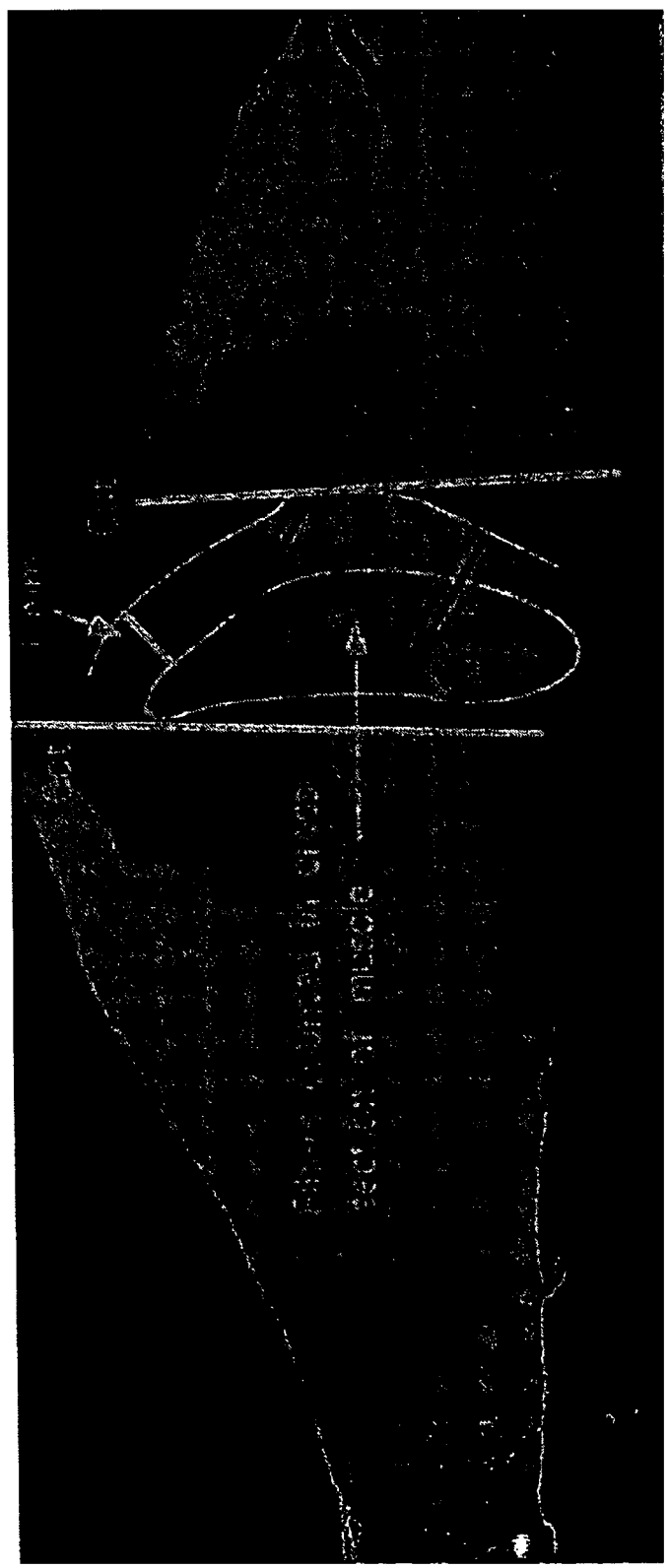
FIG. 4—pictures a whole muscle and a 1 mm slice of a transfected muscle. Dark stain indicates o-nitrophenyl-b-D-galactopyranoside (ONPG) that has been catalyzed by β-galactosidase in the muscle to yield a dark precipitate. Arrows illustrate muscle fibers that were successfully transfected using the method of the present invention.
Figure 5:
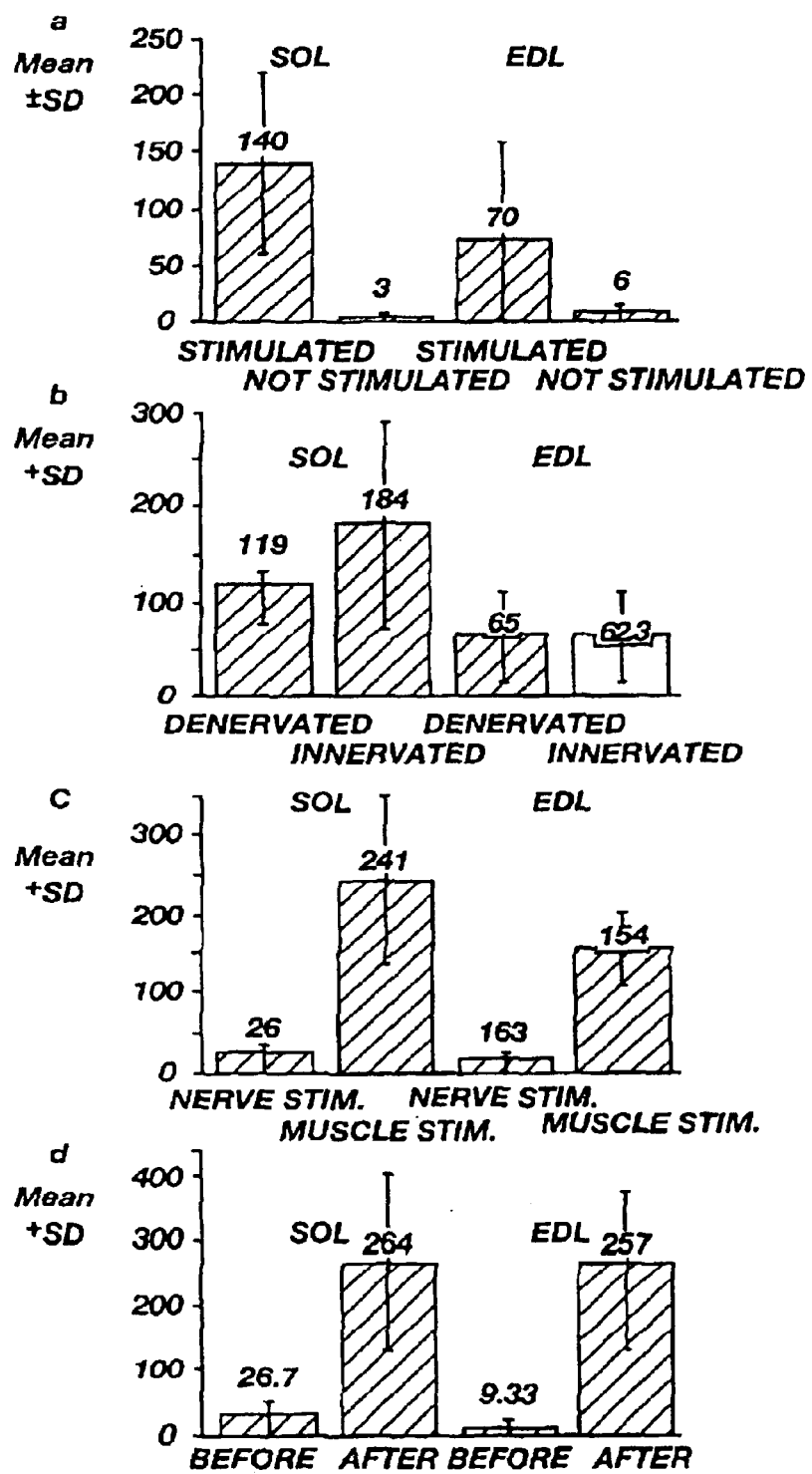
FIG. 5—includes mean number of transfected fibers from each group of skeletal muscles shown in FIG. 3.

Fifteen days after DNA injection the soleus and EDL muscles were analyzed. As illustrated in FIG. 3a, muscle cells that were stimulated immediately after DNA injection (bottom panels) contain more blue product indicating that more β-galactosidase gene was introduced into the muscle cells. The transfection efficiency was quantitated by counting the muscle fibers in a 1 mm cross section of the muscle that contained blue product as illustrated in FIG. 4. As illustrated by the bar graph in FIG. 5a, soleus muscle transfected using the method of the present invention showed a 47-fold increase over muscles that were not stimulated. Similarly, EDL muscle transfected using the method of the present invention showed a 12-fold increase over muscles that were not stimulated.

To determine whether nerve activity affected the transfection efficiency, the method of the present invention was performed on innervated (sciatic nerve not transected) and denervated (sciatic nerve transected) soleus and EDL muscles as described above. As illustrated in FIG. 3b, fifteen days after DNA injection both innervated and denervated muscles produced a generous quantity of blue product indicating high efficiency transfer of the β-galactosidase gene. As illustrated in FIG. 5b, quantitation of transfected muscle fibers confirms high efficiency transfection of both innervated and denervated muscles.

To rule out the possibility that the increased transfection efficiency observed was due to muscle activity, direct stimulation of the sciatic nerve was compared to stimulation of the muscle (n=5). If the increased transfection efficiency was due to muscle activity, the transfection efficiency in muscles stimulated via the nerve should yield similar efficiencies as direct muscle stimulation. As illustrated in FIG. 3c, direct nerve stimulation did not significantly increase transfection efficiencies compared to direct muscle stimulation. As illustrated in FIG. 5c, in both soleus and EDL muscles a 10-fold increase in transfection efficiency was observed with direct muscle stimulation.

As illustrated in FIG. 3d, the increased efficiency is transient, consistent with electroporation. Muscles stimulated directly after DNA injection display significantly more blue dye than muscles that were stimulated prior to DNA injection. In fact, muscles that were stimulated directly after DNA injection displayed transfection efficiencies between 10- and 25-fold greater than muscles that were stimulated 10 minutes prior to DNA injection (FIG. 5d).

Figure 6:
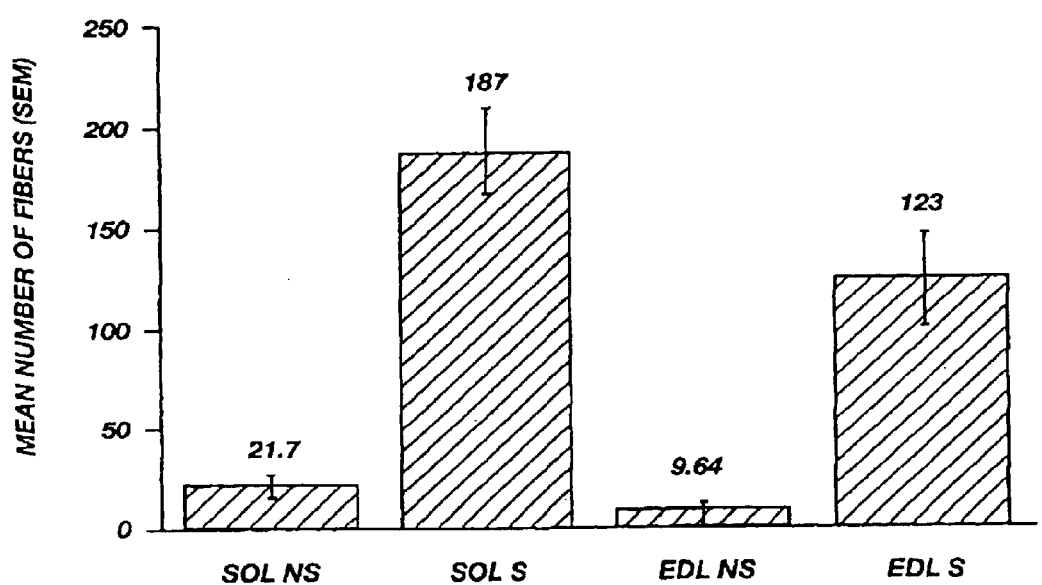
FIG. 6—is a bar graph illustrating mean transfected fibers of muscles from several different experiments and several different batches of DNA grouped together. In columns marked SOL S and EDL S the muscles (16 in each group) have been stimulated directly after the injection of DNA. In columns marked SOL NS and EDL NS the muscles (10 in each group) have been stimulated by the nerve, not stimulated at all or stimulated directly 10 minutes before the DNA injection.
Figure 7:
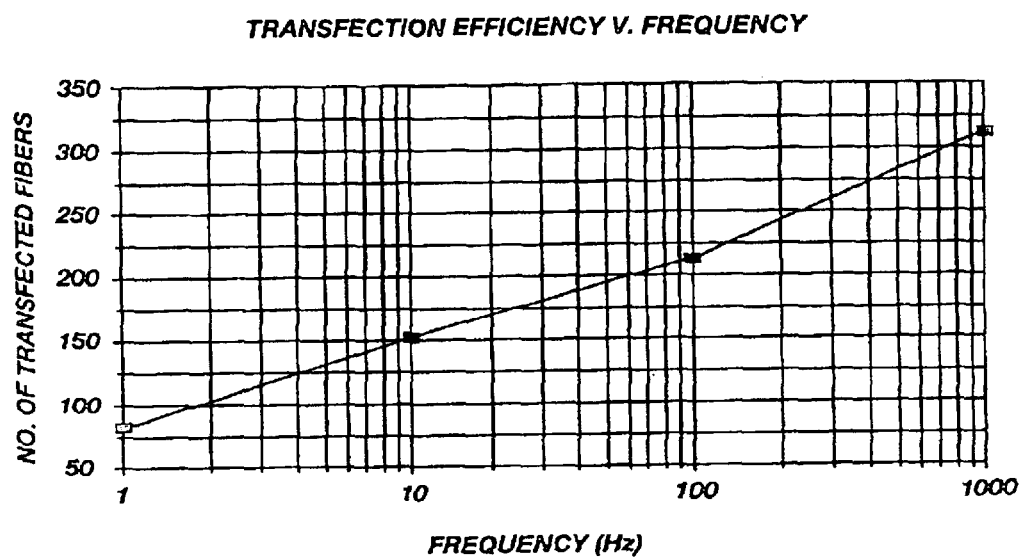
FIG. 7—is a graph illustrating the number of skeletal muscle fibers transfected versus the log of the stimulation frequency. The duration of the stimulation train was kept constant at 1 second.
Figure 8:
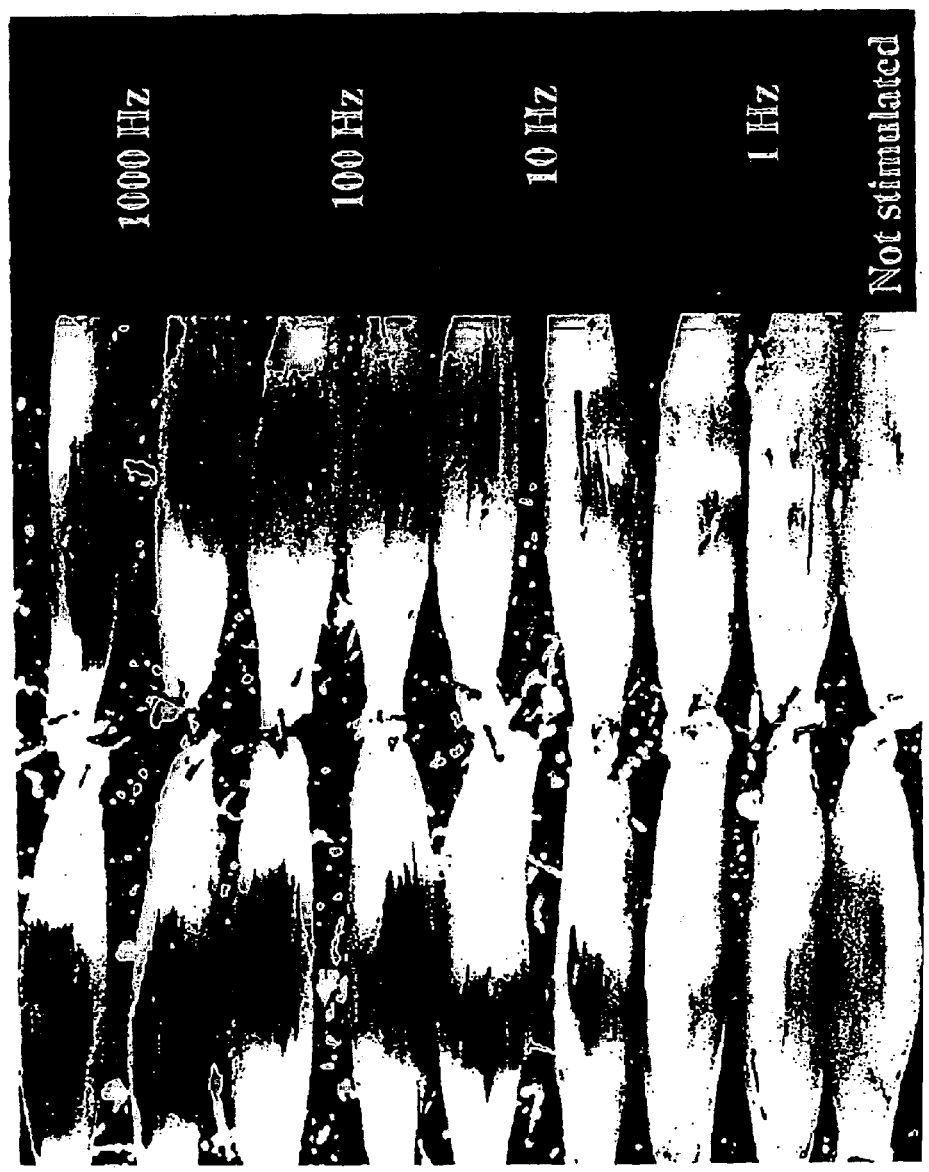
FIG. 8—is a photograph of transfected muscles from which data in FIG. 7 were generated.

FIG. 6 summarizes the results of the present invention. Muscles from several different experiments and several different batches of DNA are grouped together. In columns marked SOL S and EDL S the muscles (16 in each group) have been stimulated directly after the injection of DNA. in columns marked SOL NS and EDL NS the muscles (10 in each group) have been stimulated by the nerve, not stimulated at all, or stimulated directly 10 minutes before the DNA injection.

The electrical stimulator used for the experiments was manufactured by FHC (Brunswick, Me. 04011). Both Pulsar 6 bp and the Pulsar 6 bp-a/s stimulators have been used. The Pulsar 6 bp-a/s delivers a maximal voltage is 150 V and a maximal current of 50 mA. The maximal voltage that can be delivered requires a resistance between the electrodes of greater than 3000 ohms. The stimulators have been operated at constant voltage mode. Because of the low resistance in the muscle, the voltages have been lower as discussed in the Examples below. In all experiments the current has been maintained at 50 mA.

Figure 9:
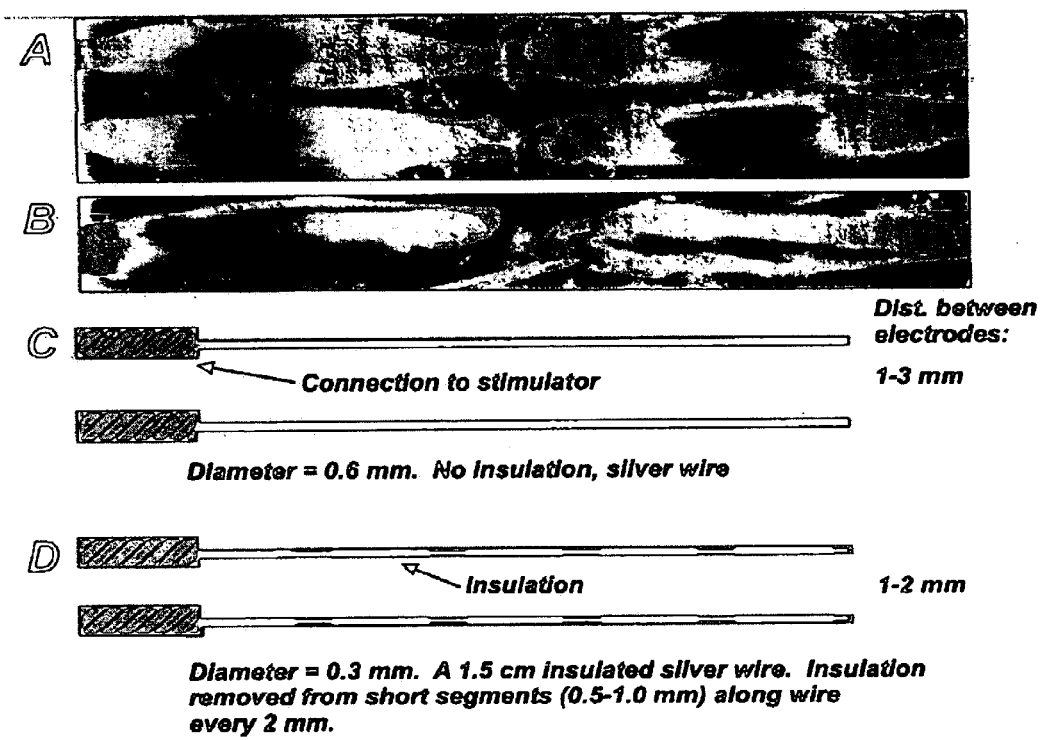
FIG. 9—illustrates the results achieved when whole mounts of muscles were transfected according to the method of the present invention using two different electrodes.

It will be appreciated by one skilled in the art that numerous other electrode configurations can be employed. For example, FIG. 9 illustrates the results obtained using two different electrodes configuration. The electrode shown in (A) was placed perpendicular to the muscle fibers. It consisted of a silver wire with diameter (d) of 0.6 mm, (C) (this is the electrode which was used in all experiments except in (B)). One electrode was placed on each side of the muscle. A short segment in the middle third of the muscle is positive for the Lac Z staining (A), indicating localized expression. In (B) a 1.5 cm electrode made from an insulated silver wire was used (d=0.3 mm). Insulation was removed from short segments (0.5–1.0 mm) along the wire at 2 mm intervals (D). The electrode was penetrated into the muscle in parallel with the muscle fibers. One of the two wires of the electrode was penetrated into the muscle parallel with the muscle fibers. The second wire was placed on the muscle surface, also parallel with the fibers. Both types of electrodes (FIGS. 9c and 9d) gave a similar number of transfected fibers (approximately 250). Using the longer electrode in parallel with the muscle fibers, however, gave a more wide spread staining, indicating a transfection along a longer segment of the fibers and/or increased transfection.

Muscles were stained for Lac Z in whole mounts by methods well known in the art. After staining, the pictures were taken with the bluest side of the muscle up. Thereafter the muscle was cut in three pieces as seen in FIG. 2. The number of blue fibers in about 1 mm thick slice from the middle of the muscle were counted (fibers transfected distally or proximally from the slice are therefore not counted). In order to count the transfected fibers, the slices were dissected into smaller bundles so single fibers could be distinguished under a dissection microscope.

In four (4) muscles the pSV40-luc construct was used. It was injected into the soleus muscle, 3 days after the muscles were removed and luciferace activity was measured using the Promega Luciferace Assay System (Daviset et al., 1993). Uninjected EDL from the same rats were used as control.

It will be appreciated that any nucleic acid can be used with the method of the present invention, for example, plasmid DNA, linear DNA, antisense DNA and RNA. In one preferred embodiment, the nucleic acid is a DNA expression vector of the type well known in the art. Generally, an expression vector contains a promoter operably linked to a DNA molecule that codes for the protein of interest followed by a termination signal such as a polyadenylation signal. Other elements required for bacterial growth and proper mammalian processing may be included, such as the β-lactamase coding region, an f1 origin and ColE1-derived plasmid replication origin. Similar constructs containing a DNA coding region of interest can be constructed by one skilled in the art.

As illustrated in the examples below, molecules other than nucleic acids can be delivered to the muscle using the technique of the present invention. In one embodiment, rhodamin conjugated dextran injected into the muscles and stimulated according to the method of the present invention was able to enter muscle cells. In addition, nucleic acid and proteins can be simultaneously introduced into an electroporated muscle. In one embodiment, the large T-antigen nuclear localization signal was mixed with a plasmid containing the DNA coding region for Lac Z. The large T-antigen nuclear localization signal is a protein that binds DNA and facilitates its transport into the nucleus of a cell. In other systems, large T-antigen nuclear localization signal has been shown to increase transfection efficiency. Using the method of the present invention, large T-antigen nuclear localization signal also increased the transfection efficiency of Lac Z indicating that the protein was able to bind the DNA and enter the muscle cell.

The method of the present invention can be used to drive the immune response of an animal in a specific direction. For example, DNA encoding for an antigen was administered to a group of mice according to the method of the invention. After four and eight weeks, serum was collected from the mice and antibodies analyzed by ELISA. The mice had a high level of IgG2a antibodies that reacted with the antigen, indicating that a strong cellular immune response was induced. When animals were immunized according to the method, increased number of CD8+ and CD4+ T-cells that secreted interferon gamma was measured with ELISPOT after stimulation with peptides specific for MHC I and II binding. This demonstrate a strong cellular immune response as well as induction of Th-1 cells. When animals were given a boost injection in combination with a reporter gene a reduced expression of reporter gene indicating a stronger cellular immune response was observed in animals that had been immunized according to the present invention.

Another example is to drive the immune response in the other direction with preferential stimulation of the humoral branch of the immune system. When protein was used in accordance with the present invention, higher IgG1 and IgG2b antibody titers could be detected. When these protein-treated animals were given a boost injection of protein in combination with a reporter gene, increased expression of the reporter gene was observed. These results indicate that immunization with protein in combination with electrical stimulation had altered the immune response in such a way as to make the animals tolerant to the antigen. Alternatively, such immunization may stimulate an immune reaction that is not efficient in killing muscle cells. This method may be useful for the treatment of various autoimmune diseases in which a strong cellular immune response causes or contributes to the disease.

Without being bound by any particular theory, one mechanism to explain these results could be that other cells in addition to skeletal muscle cells can be transfected by the method of the present invention. For example, animals were intramuscularly injected with Luc cDNA. The muscles were electrically stimulated shortly after the injection. Animals were sacrificed at two and seven days, and their spleens and lymph nodes removed and analyzed for luciferace activity. As shown in Table 5 below and FIGS. 22 & 23, a large increase in luciferace activity in the lymph nodes and spleen was found. These findings indicate that immune cells residing within the muscle are transfected by the method of the present invention.

Local anaesthetics are frequently used in medical procedures to reduce the pain and anxiety caused by the procedure. Marcain (2.5 mg/ml from Astra, bupivacain hydroclorid) is one such local anaesthetic. Marcain may be mixed with DNA to reduce the possible discomfort of muscle stimulation associated with electroporation. As seen in FIGS. 24 through 27, the administration of Marcain had no significant effect on either the resulting immune response or the transfection efficiency. For this procedure, a high concentration of Marcain was used. However, it would be appreciated by those of skill in the art that other concentrations of Marcain and other anaesthetics can be used without departing from the nature of the present invention.

Figure 30:
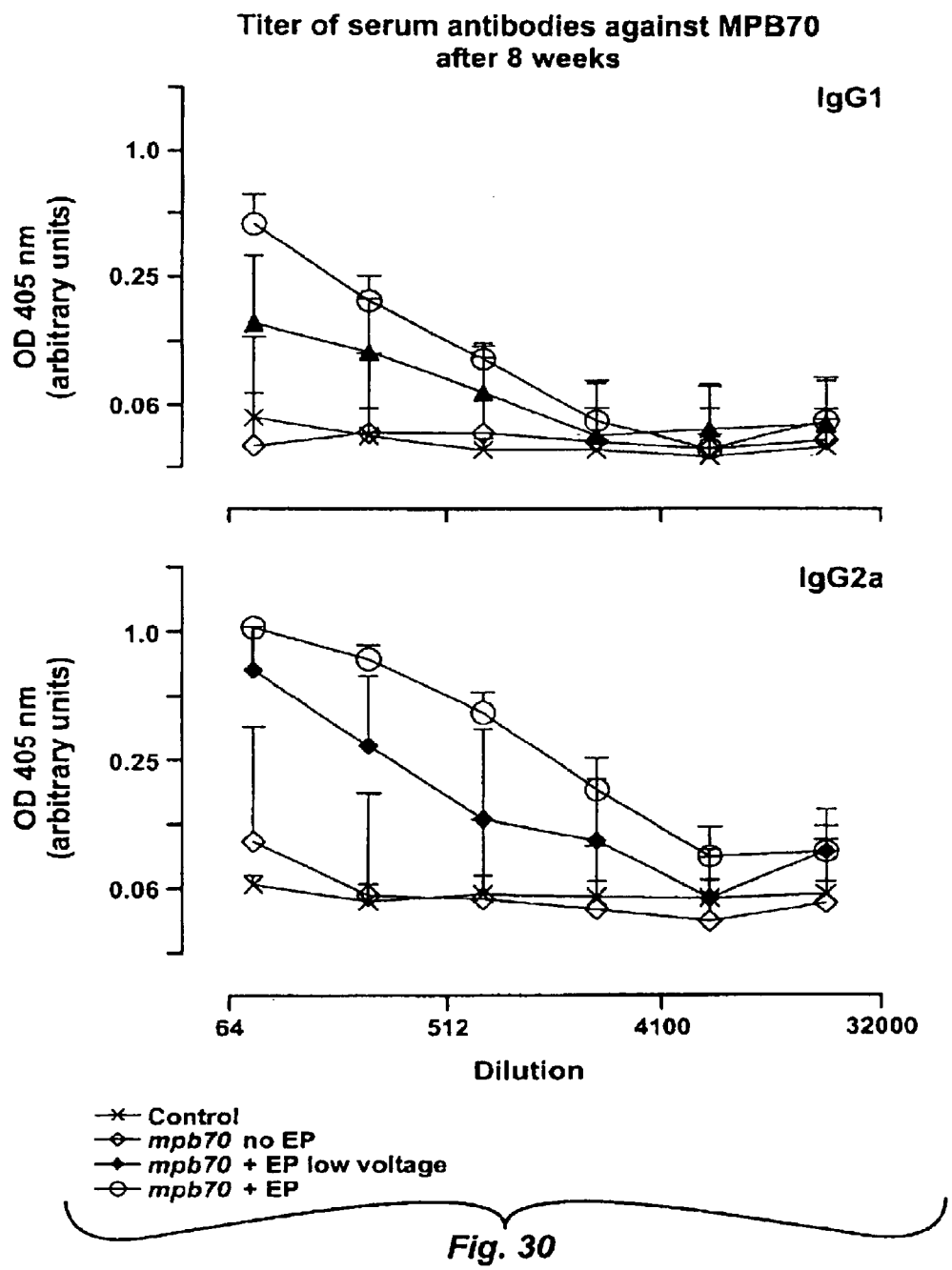
FIG. 30—are graphs illustrating antibody levels in mice eight weeks after genetic immunization with low electrical field strength.

One may transfect the cells residing in the skeletal muscle using low electrical field strength, i.e., less than approximately 100 V/cm. In certain embodiments, cells within the muscle are transfected with a field strength of at least about 5 V/cm. In certain other embodiments, cells within the muscle are transfected with a field strength of at least about 10 V/cm. For example DNA encoding an antigen was administered according to the method of the invention and the muscle was stimulated with a field strength of about 10 V/cm to about 25 V/cm. As seen in FIG. 30, a large increase in antibodies against the antigen were detected for low voltage stimulation as compared to injected naked DNA. One might also use much greater field strengths. For example, one could transfect cells within muscle using field strengths in the range of from approximately 10 V/cm to approximately 300 V/cm. In certain embodiments of the present invention, one could transfect cells within muscle using field strengths of from approximately 12 V/cm to approximately 175 V/cm; from approximately 125 V/cm to approximately 233 V/cm; or from approximately 10 V/cm to approximately 233 V/cm.

One skilled in the art would appreciate that a boost injection (immunization) given subsequent to the first immunization is likely to enhance the immune response further. This can be done with electroporation or with other immunization strategies. For example, animals have been immunized with plasmid DNA and then later with a certain virus encoding the same antigen in order to obtain a further increase in the cellular immune response. See, e.g., Schneider et al., *Nature Medicine* 4:397 (1998). The boost injection may be given soon after the initial immunization (i.e., within a few days or a week). One skilled in the art would also appreciate that booster immunizations may be given many years after the first injection. In certain embodiments of the present invention, boost injections are given at a time from about two weeks to about four months after the initial immunization. In certain preferred embodiments, boost injections are given at a time from about one month to about two months after the initial immunization.

Without being bound by theory we have several possibilities for why EP enhances the immune response; first EP enhances expression of the antigen, second it enhances expression in other cells that are later found in lymphnodes or spleen, third it seem to enhance the muscles cells ability to present antigen (MHC class I staining), fourth; electrical stimulation will cause muscle activity that is likely to increase the lymphflow from the muscles (f.ex. low voltage stimulation). The mechanism are probably due to many of these factors in combination and the contribution of each and one of them will depend on the type of immune response being induced.

EXAMPLES

The following examples are given to illustrate various embodiments which have been made of the present invention. It is to be understood that the following examples are not comprehensive or exhaustive of the many types of embodiments which can be prepared in accordance with the present invention.

Example 1

Stimulated Versus Unstimulated Muscles

Transfection efficiencies were determined by injecting skeletal muscles with the pSV40-luc reporter construct into the soleus muscle. Three days after injection, the muscles were removed and luciferace activity was measured using the Promega Luciferace Assay System (Madison, Wis.) according to manufacturer's protocols. Unstimulated EDL muscles from the same rates were used as control. The data are shown below in Table 1.

TABLE 1

| Muscle | Stimulated (Relative luciferace-activity) | Unstimulated (Relative luciferace activity) | Percent Increase |
|---|---|---|---|
| Soleus animal I | 34.40 | 1.950 | 1664% |
| Soleus animal II | 21.50 | 0.250 | 8500% |
| EDL animal I |  | 0.045 |  |
| EDL animal II |  | 0.046 |  |

Example 2

Transfection Efficiency Versus Frequency

Rats were injected with 50 µl of 1 mg/µl of a plasmid carrying lac Z gene. Immediately following injection, electrodes were placed between 2–3 mm apart and the muscle was stimulated with the following stimulation parameters: voltage=30 volts; pulse duration=0.2 ms (total 0.4 ms, bipolar); trains=30, 1 second on 1 second off for 1 minute. Transfected fibers were counted from a 1 mm slice from middle of muscle. The number of transfected fibers is shown below in Table 2 and illustrated in FIG. 7. These data also illustrate that the method of the present invention transfects more than just surface muscle fibers; muscle fibers several cell layers deep are also transfected.

TABLE 2

TRANSFECTION EFFICIENCY VERSUS FREQUENCY

| Frequency (Hz) | Mean (Transfected Fibers) | Percent Increase with Stimulation |
|---|---|---|
| 0 | 22 | — |
| 1 | 83 | 277% |
| 10 | 153 | 595% |
| 100 | 215 | 877% |
| 1000 | 315 | 1332% |

Example 3

Transfection Efficiency Versus Pulses

Soleus muscles of Wistar rats (200–270 grams) were injected with 50 µg of RSV luciferace DNA plasmid in 50 µl 0.9% NaCl. Shortly after injection, the muscles were electrically stimulated using the following parameters: 1000 Hz, between 0–1000 bipolar pulses of 200 µs duration in each train were applied to the muscle 30 times over a period of 1 minute.

Figure 10:
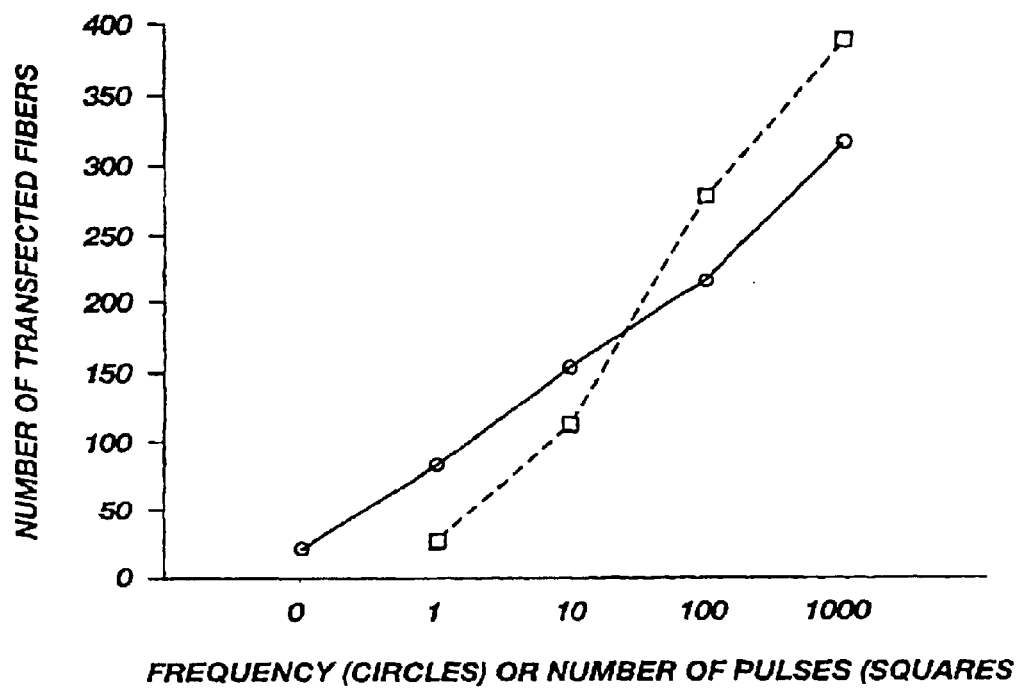
FIG. 10—is a graph illustrating the number of skeletal muscle fibers transfected with increasing frequency compared to increasing pulse number.
Figure 11:
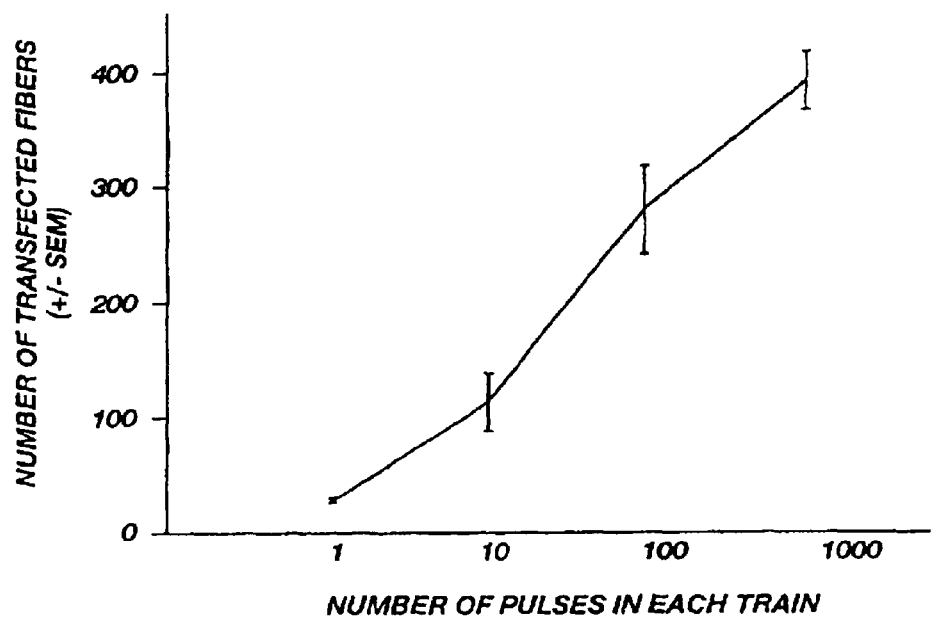
FIG. 11—is a graph illustration of the number of skeletal muscle fibers transfected versus the number of pulses at constant frequency.
Figure 12:
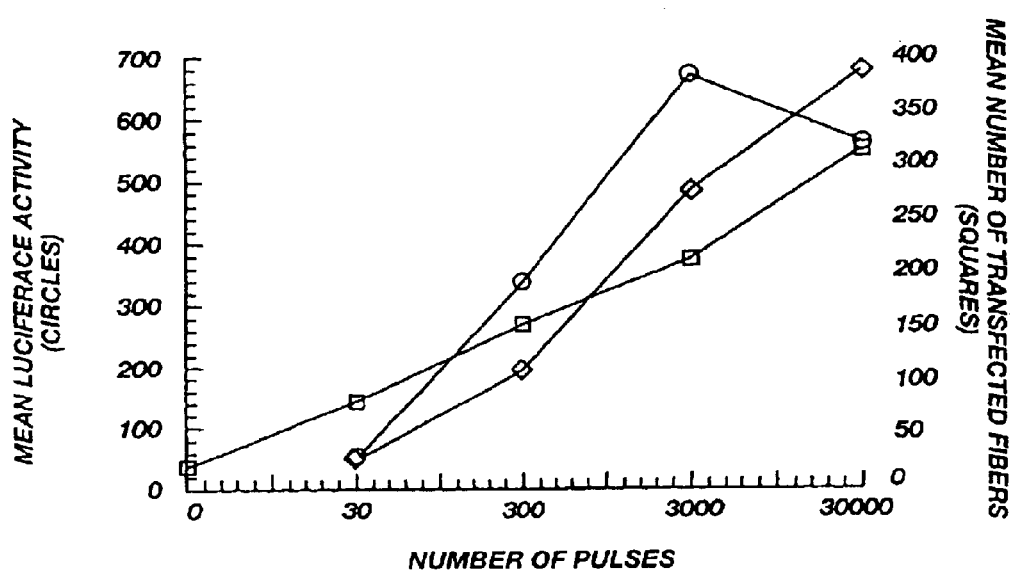
FIG. 12—is a graph illustrating mean luciferace activity versus the number of pulses.

Muscles were removed 3 days after transfection and frozen in liquid nitrogen. Cryostat sections were taken from the of the muscles and stained with Hematoxolin, Eosin and Safran (see Example 9). The remaining pieces were homogenized as described in Example 4 below. As illustrated in FIGS. 10–12, transfection efficiency increased with the number of pulses delivered to the muscle.

Example 4

Determining the Effect of Voltage on Transfection Efficiency

EDL and soleus muscles of Wistar rats (245–263 grams) were injected with 25 µg of RSV driven luciferace plasmid DNA in 50 µl 0.9% NaCl. Shortly after injection, the injected muscles were electrically stimulated using the following parameters: 100 Hz, 100 bipolar pulses in each train of 200 µs duration, voltage varied from between 0 to 47.5. Muscles were removed 4 days post injection and stimulation, homogenized in Promega (Madison, Wis.) luciferace assay buffer and luminescence was measured according to manufacturer's protocols. Macintosh computer and a LabWiev acquisition program were used to capture the first voltage pulses. Recordings were done in parallel with the stimulation electrodes. The voltage measurements were done manually on prints as the average of the maximal voltage of 10 pulses approximately 100 ms after onset of stimulation.

Figure 13A:
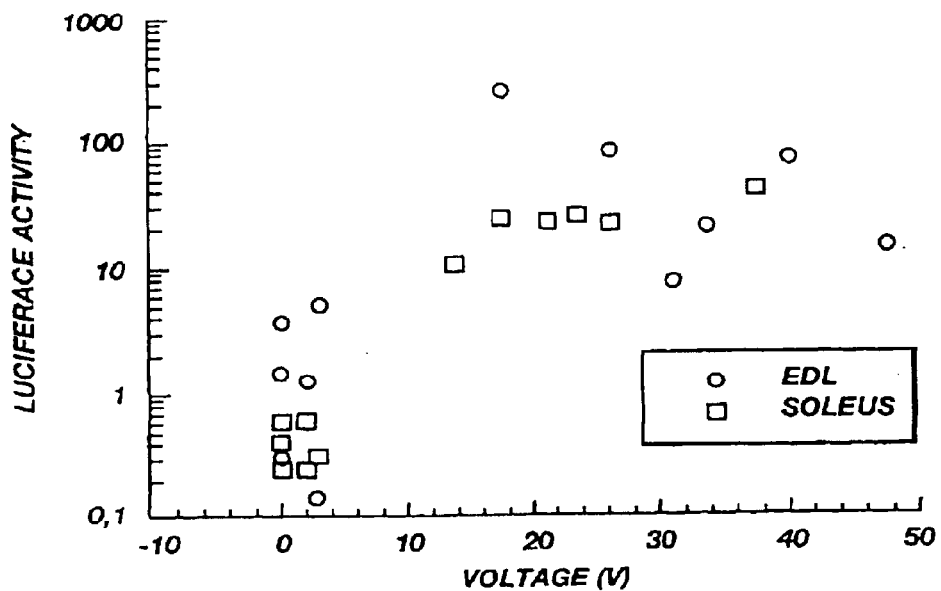
FIG. 13a illustrates the luciferace activity of muscle stimulated with varying volts.
Figure 13B:
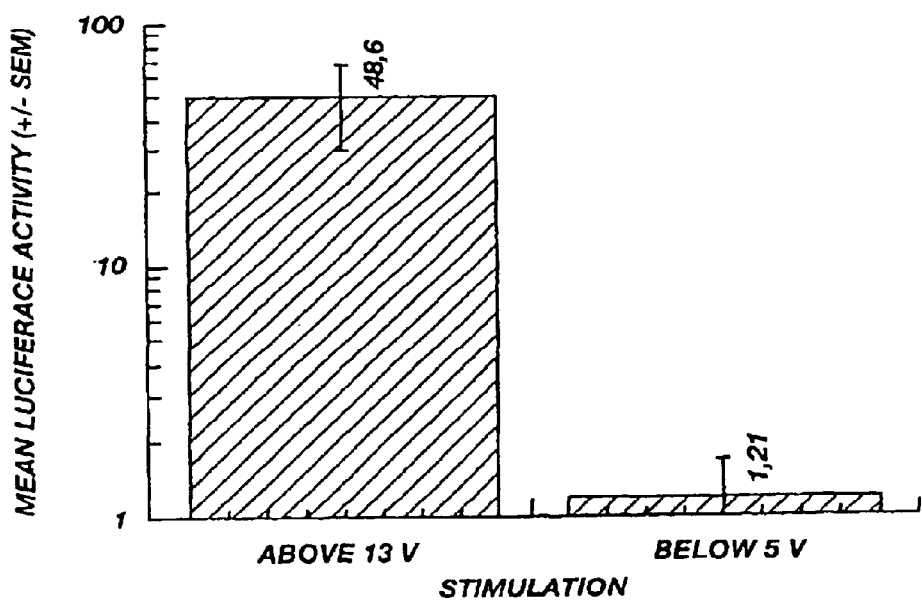
FIG. 13b illustrates the mean luciferace activity of muscles stimulated with an amplitude above 13 volts and below 5 volts.

As illustrated in FIG. 13a, there was a pronounced increase in transfection efficiency with increased voltage. As illustrated in FIG. 13b, under the conditions of this experiment, muscles stimulated with 13 volts or higher showed 40-fold greater luciferace activity compared to muscles stimulated with 5 volts or less.

Example 5

Determining Optimal Pulse Duration

Figure 14:
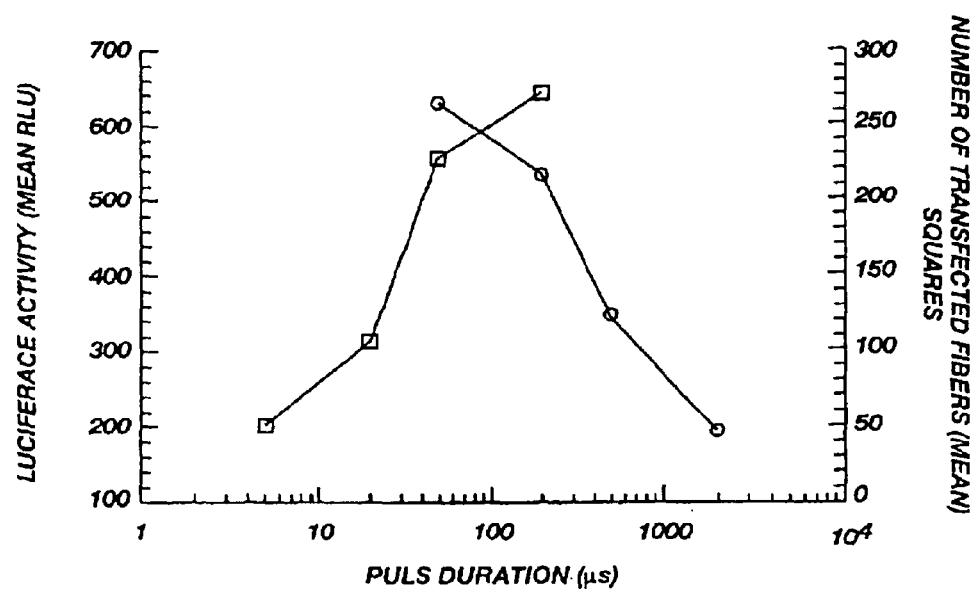
FIG. 14—is a graph illustrating the effect of pulse duration on the transfection efficiency.

Soleus DNA plasmid containing the β-galactosidase gene in 50 µl 0.9% NaCl. Shortly after injection, the muscles were electrically stimulated using the following parameters: 100 Hz, 25 volts, 100 bipolar pulses in each train having pulse durations ranging from 5–200 μs. The number of transfected fibers were counted in a 1 mm thick section from the middle of the muscle under a dissection microscope. A second set of rats were injected with 25 μg of RSV-driven luciferace plasmid DNA in 50 μl 0.9% NaCl and electrically stimulated with the same parameters as above except that the pulse durations were varied from 50–2000 μs. As illustrated in Table 3 below and FIG. 14, under these stimulation parameters, the optimal pulse duration ranged from about 50 μs to about 200 μs. This method can be used to optimize the pulse duration of other stimulation parameters.

TABLE 3

TRANSFECTION EFFICIENCY VERSUS PULSE DURATION

| Pulse Duration (μs) | Transfected Fibers (Mean) | Pulse Duration (μs) | Luciferace-activity (Mean) |
| --- | --- | --- | --- |
| 0 | — | 0 | 52.7 |
| 5 | 51 | 50 | 631 |
| 20 | 107 | 200 | 536 |
| 50 | 228 | 500 | 348 |
| 200 | 272 | 2000 | 194 |

Example 6

Current Versus Number of Pulses

Figure 15:
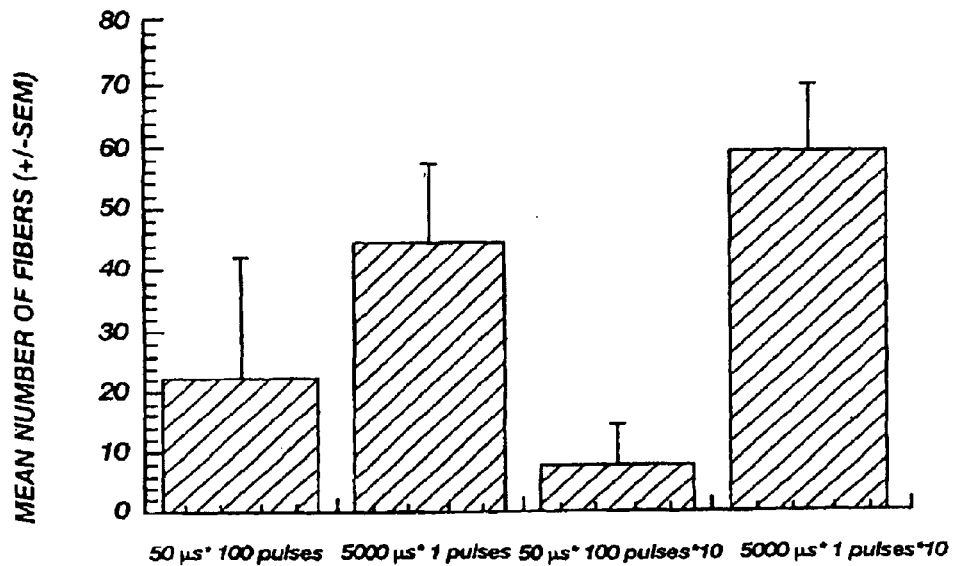
FIG. 15—is a bar graph illustrating a comparison of transfection efficiencies for varying pulse durations and pulse numbers.

Soleus muscles of six Wistar rats (178–193 grams) were injected with 50 μg of DNA plasmid containing the β-galactosidase gene in 50 μl 0.9% NaCl. Shortly after injection, the muscles were electrically stimulated as described above except that the pulse duration was varied. The following electroporation parameters were compared: (1) 100 pulses of 50 μs duration versus 1 pulse of 5000 μs; and (2) 10 trains of 100 pulses of 50 μs versus 10 pulses of 5000 μs. Muscles were removed 14 days later and sectioned on a cryostat. Cross sections were stained as previously described. The number of transfected fibers were counted. As illustrated in FIG. 15, longer pulse durations result in higher transfection efficiency.

Example 7

DNA Concentration

Figure 16:
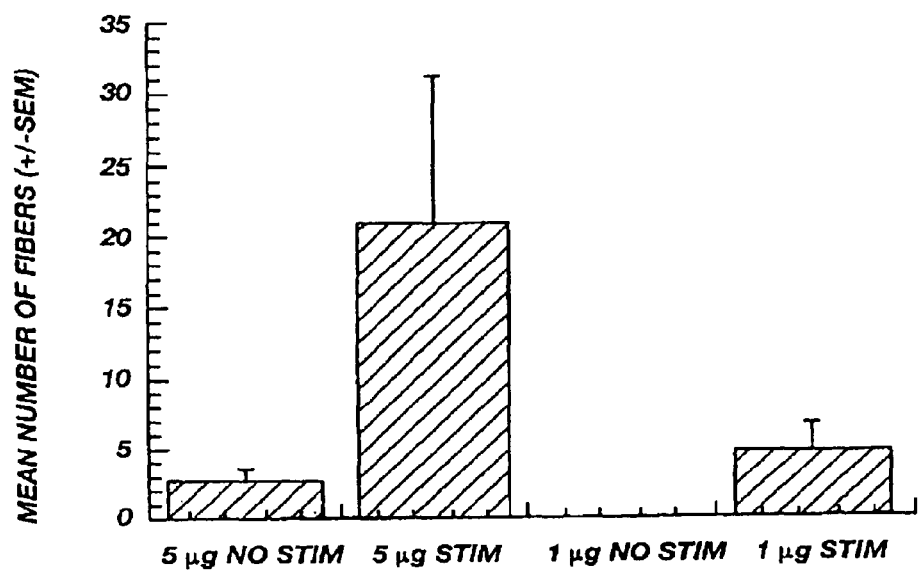
FIG. 16—is a bar graph illustrating the effect of DNA concentration on transfection efficiency.

EDL muscles of six Wistar rats (178–193 grams) were injected with either 1 μg/μl or 5μ/μl of DNA plasmid containing the β-galactosidase gene in 50 μl 0.9% NaCl. Shortly after injection, the muscles were electrically stimulated with 30 trains of 100 pulses of 200 μs duration or not stimulated at all. Muscles were removed 14 days later and sectioned on a cryostat. Cross sections were stained as previously described and transfected fibers were counted. As illustrated in FIG. 16, greater transfection efficiencies were obtained with higher DNA concentrations.

Example 8

Large T Antigen Nuclear Localization Signal

Wistar rat muscles were injected with DNA plasmid containing the β-galactosidase gene containing a 100:1 molar excess of large T-antigen nuclear localization signal. This has been shown in other transfection studies to improve the transfection. See, Collas et al. *Transgenic Res.* 6:451–8 (1996). The muscle were stimulated with 10 trains of 100 pulses of 50 μs duration. The muscles containing the large T-antigen nuclear localization signal had the highest number of transfected fibers. Specifically, the muscle co-transfected with large T-antigen nuclear localization signal had 100 and 38 transfected fibers versus 7.3 and 4.7 for the muscles transfected only with DNA, respectively. These data illustrate that transfection efficiencies can be aided by mixing the DNA with non-nucleic acid molecules. In addition, this data illustrates that non-nucleic acid molecules can also be delivered to the muscle using the electroporation techniques of the present invention. No improvement was seen in cells that were not stimulated following injection.

Example 9

Muscle Damage Resulting from Stimulation

Figure 17A:
FIG. 17a illustrates an injected muscle that was not stimulated.
Figure 17B:
FIG. 17b illustrates muscle damage following muscle stimulation.
Figure 17C:
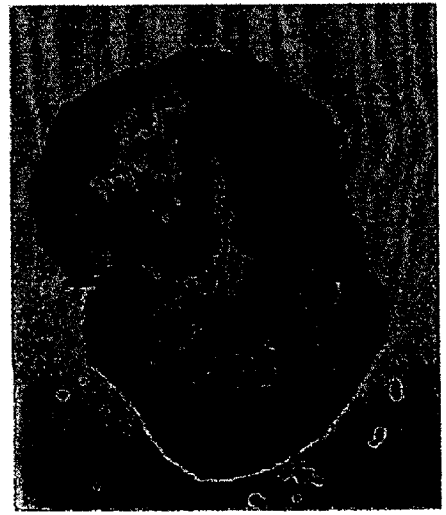
FIG. 17c illustrates muscle stimulated under harsher stimulation conditions.
Figure 17D:
FIG. 17d illustrates that muscles stimulated under the conditions of muscles in 17c are completely regenerated and repaired after 14 days.

Muscles from Example 3 that were sectioned and stained to assess the muscle damage from electroporation. As illustrated in FIG. 17*a*, some damage can occur with injection alone, although the majority of unstimulated muscles were undamaged. In muscles stimulated with 300 pulses, more damage was observed (FIG. 17*b*). As illustrated in FIG. 17*c*, muscle stimulated with 30 trains of 1000 pulses displayed greater damage, indicating that damage is proportional to the extent of stimulation. FIG. 17*d* illustrates that muscles stimulated under the conditions of muscles in 17*c* are completely regenerated and repaired after 14 days.

Figure 17E:
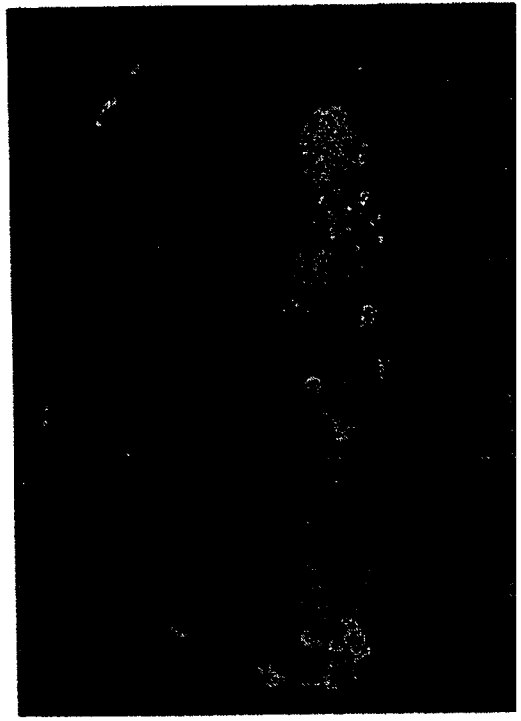
FIG. 17e illustrates muscles transfected with green fluorescent protein (GFP).
Figure 17F:
FIG. 17f illustrates that transfected fibers can bee seen in the vicinity of the damaged area.

In another muscle which got the highest amount of stimulation (30 trains of 1000 pulses), plasmid DNA encoding green fluorescent protein (GFP), was also included. FIG. 17*e* illustrates muscles transfected with GFP. Transfected fibers can bee seen in the vicinity of the damaged area (FIG. 17*f*). Transfected regenerating fibers were never observed in cross sections 3 days after electroporation.

Example 10

Genetic Immunization of Rabbits

A female rabbit (4.5 kg) was injected into the right femuralis rectus with 2 milliliters of 1 μ/μl of DNA plasmid containing the rat neural agrin cDNA driven by the CMV promotor (Cohen et al. MCN, 9, 237–53 (1997)). The first milliliter was injected equally in ten places superficial in the muscle followed by 10 trains of 1000 pulses delivered at a frequency of 1000 Hz. The second milliliter was placed further down in the muscle. To test the rabbit serum, rat muscles and COS cells were transfected with the same construct. Muscles were taken out 5 days after transfection and the COS cells were stained 4 days after transfection.

Bleeds were collected at days 0, 19, 50, 81 and 106 and diluted 1:100 and 1:1000. After 19 days the bleed contained enough antibody in the serum to give a weak staining of transfected fibers when diluted 1:10. As a positive control the monoclonal antibody (mAb) AG-86 was used. See Hoch et al. *EMBO J,* 12 (13): 2814–21(1994). Preimmune serum did not show any staining of transfected fibers. Later bleeds all had agrin antibodies in the serum. Bleed collected at day 50 or later contained sufficient antibodies to stained sections at a dilution of 1:1000.

Figure 18A:
FIG. 18—is a photograph of cells stained with anti-agrin polyclonal antibodies derived from a rabbit genetically immunized with an expression vector coding for rat agrin using the stimulation technique of the present invention.
Figure 18B:
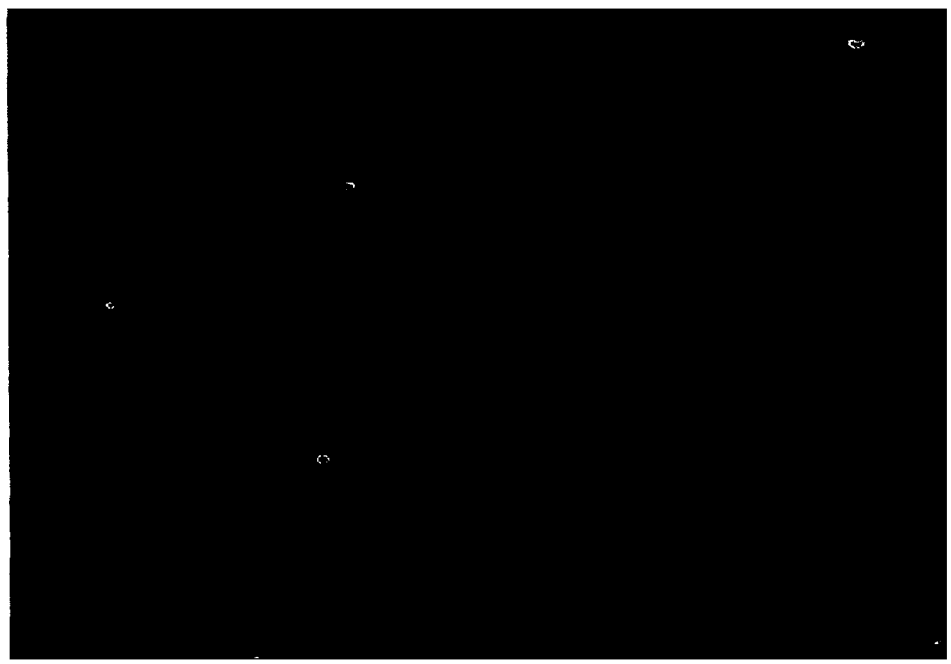
Figure 18C:
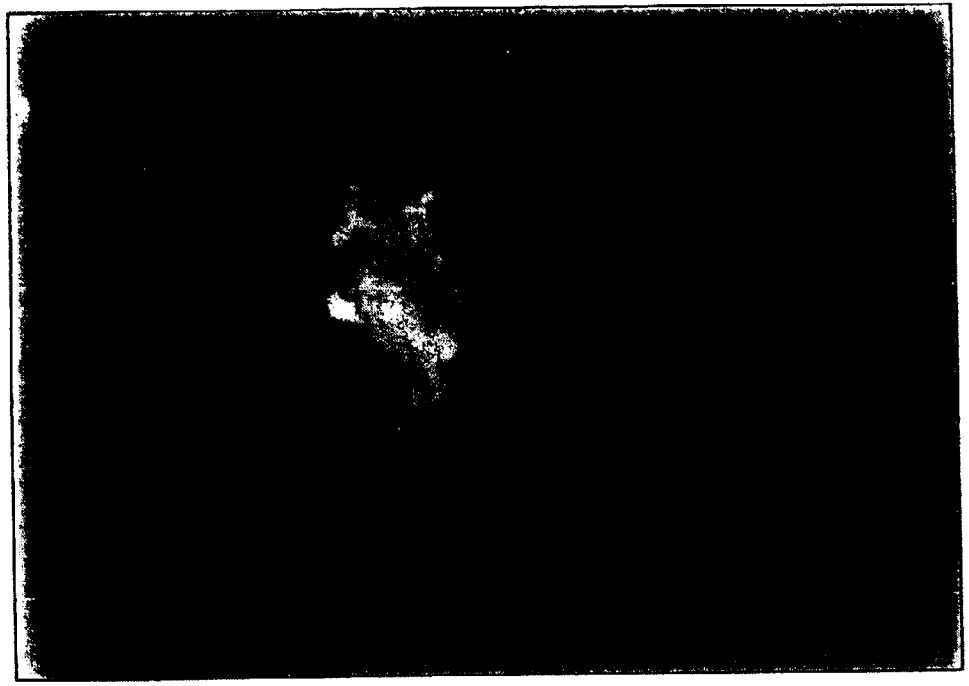
Figure 18D:

FIG. 18*a* illustrates the agrin transfected COS cells stained with antiserum from immunized rabbit (diluted 1:100) and fluorescein conjugated secondary antibody. COS cells were stained first fixing the cells in 1.5% paraformaldehyde for 10 minutes, followed by a 30 minute wash with phosphate buffered saline (PBS). The cells were then blocked with 0.2% bovine serum albumin, triton X-100, 0.1% in PBS 0.1M, for 4 minutes. Serum diluted in same solution was added to the cells and allowed to incubate for 20 minutes. Cells were wash for 4 minutes in PBS and incubated with the secondary antibody (Cappel, 55646) for 10 minutes followed by a PBS wash. Mouse primary mAb Agr-86 was included in the same antibody mixture and rhodamin conjugated secondary antibody (Sigma T-5393, St. Louis, Mo.) was used at a dilution of 1:100. FIG. 18b illustrates the same cells stained with mAb Ag-86/rhodamin conjugate. These data illustrate the potential of the technique of the present invention for genetic immunization or DNA vaccine technology.

Example 11

Genetic Immunization of Mice

Groups of two-month old male Sprague Dawley rats were inoculated bilaterally in the EDL and soleus muscles with a total of 200 micrograms (4×50 microliters of a 1 mg/ml solution of DNA in saline) of three different eukaryotic expression vectors containing the cytomegalovirus immediate early promoter (CMV) and the coding sequences for the following proteins: DH-CNTF, an agonistic variant of human ciliary neurotrophic factor (Saggio et al. EMBO J. 14, 3045–3054, 1995); AADH-CNTF, an antagonistic variant of human ciliary neurotrophic factor (Di Marco et al. Proc. Natl. Acad. Sci. USA 93, 9247–9252, 1996); sec-DHCNTF, a secreted form of DH-CNTF. The muscles were either not electrically stimulated or stimulated immediately after DNA injection using 30 trains of 100 or 1000 square bipolar pulses (duration 200 microseconds; amplitude setting 150 V, effective voltage ~25 V) each, delivered at a frequency of 1000 Hz with a two second interval between successive trains.

Groups of two-month old male CD1 mice were inoculated bilaterally in the quadriceps muscles with 100 micrograms (2×50 microliters of a 1 mg/ml solution of DNA in saline) of sec-DHCNTF plasmid, with or without electrical stimulation of the muscle immediately after DNA injection. Stimulation conditions were 10 trains of 1000 square bipolar pulses (amplitude setting 150 V) delivered at a frequency of 1000 Hz with a two second interval between successive trains.

Blood was collected from the retroorbital sinus at selected time points and serum was prepared and stored at −20° C. The presence of anti-CNTF antibodies in rat and mouse sera was determined by ELISA. Microtiter plates coated with recombinant human CNTF were incubated with serial dilutions of sera, followed by alkaline phosphatase-conjugated antibody against rat or mouse IgG (Pierce). The plates were then incubated in the presence of p-nitrophenyl-phosphate and the absorbance at 405 nm was determined using a microplate reader. Antibody titers were defined as the dilution of serum producing an absorbance reading equal to 50% of that obtained with a saturating concentration of anti-CNTF antiserum.

Figure 19:
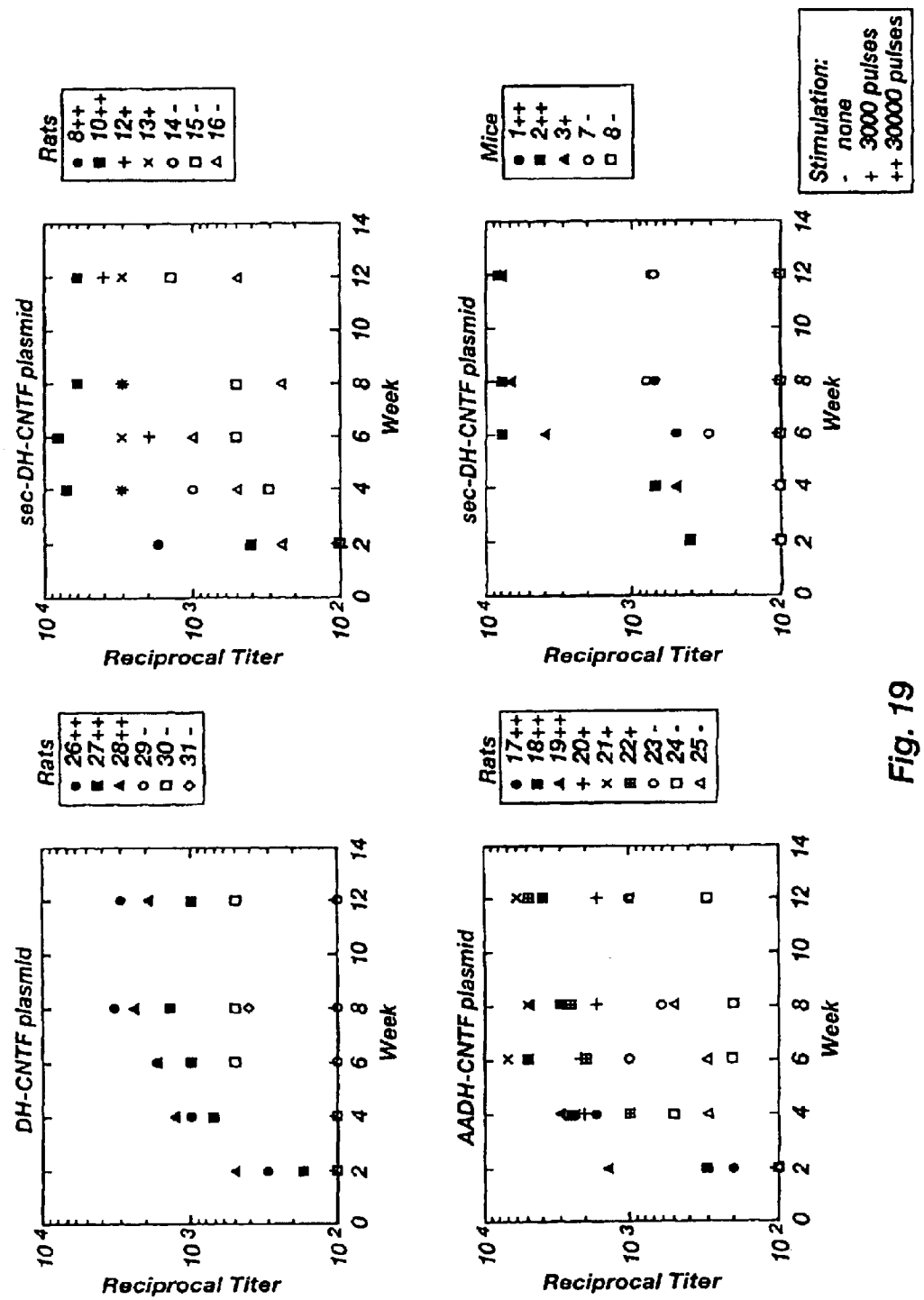
FIG. 19—are graphs illustrating improved genetic immunization of mice and rats using the stimulation technique of the present invention versus naked DNA injection.

The results are shown in FIG. 19. Titers could not be averaged with precision, due to the fact that some animals did not develop detectable amounts of antibody. Data are therefore presented for individual animals, with a value of 1:100 representing a low or undetectable antibody titer (reciprocal titer ¾ 100). The results were similar for all plasmids used, as well as for rats and mice, as depicted in FIG. 19. Similar results were also obtained in both rats and mice with another plasmid encoding an unrelated viral protein (data not shown). In both rats and mice, electrical stimulation immediately after DNA injection led to approximately 5 to 10-fold higher antibody titers than simple DNA injection. This was true for stimulation with both high and low numbers of pulses. These results demonstrate that the electroporation method increases the efficiency of DNA-mediated immunization.

Example 12

Secreted Proteins with Systemic Biological Activity

Fifty micrograms (50 microliter of a 1 mg/ml solution in 0.9% NaCl) of a eukaryotic expression plasmid (CMV-EPO) containing the cDNA of mouse erythropoietin under the control of the cytomegalovirus immediate early promoter was injected in the left quadriceps muscle of three-month old 129×Balb/C female mice. In five mice (group 1), the muscles were electrically stimulated immediately after DNA injection using 10 trains of 1000 square bipolar pulses of 200 microseconds duration, with an interval of 2 seconds between successive trains. The frequency of the trains was 1000 Hz and the amplitude set at 150 V (effective voltage ~25 V). In another group of 5 mice (group 2) the muscles were not stimulated after DNA injection. As a control, a group of 4 mice (group 3) was injected with a plasmid (CMV-GFP) containing the coding sequence for green fluorescence protein under the control of the CMV promoter, followed by electrical stimulation at the same conditions as group 1. Group 4 consisted of 5 mice injected only with saline solution without electrical stimulation.

Blood was collected from the retroorbital sinus at selected time points and hematocrit was measured by centrifugation in capillary tubes. Serum samples were analyzed for the presence of EPO using a commercial ELISA kit (R&D Systems). The results are shown in Table 4. In all groups of mice, except those that were injected with the EPO construct and electrically stimulated immediately thereafter, circulating EPO levels were below the limit of detection of the ELISA kit (<15 mU/ml). In contrast, mice injected with the EPO construct and electrically stimulated had significantly elevated serum EPO levels 5 days after injection (average of approximately 50 mU/ml). The serum concentration of EPO remained elevated for up to 28 days following DNA injection (latest time point examined; data not shown). These levels of EPO produced an increase in hematocrits, which rose from 46.2% prior to injection to 70.0% and 76.7% at 14 and 28 days after DNA injection, respectively. These values were significantly different from those obtained with both control groups (groups 3 and 4) and from those of mice injected with the EPO expression vector without electrical stimulation of the muscle (group 2). Indeed, the latter had hematocrit levels not significantly different from those of the control groups (see Table 4). These results demonstrate that the electroporation method is superior to simple DNA injection both in terms of the expression levels of a secreted protein and in producing a biological effect mediated by the secreted protein.

TABLE 4

EPO SERUM CONCENTRATIONS AND ACTIVITY

| | Mouse No. | Day 2 HCT % | Day 2 mEPO (mU/ml) | Day 5 HCT % | Day 5 mEPO (mU/ml) | Day 14 HCT % | Day 14 mEPO (mU/ml) |
|---|---|---|---|---|---|---|---|
| Group 1 CMV-EPO Stimulated | 7 | 45 | ND | ND | 55.7 | 71 | 72.4 |
| | 8 | 48 | ND | ND | 54.6 | 68 | 5.3 |
| | 9 | 47 | ND | ND | 59 | 75.5 | 48.7 |
| | 10 | 44 | ND | ND | 62.2 | 69.5 | 62.9 |
| | 11 | 47 | ND | ND | 7.9 | 66 | 22.4 |
| | Avg. | 46.2 | | | 47.9 | 70.0[abc] | 48.3 |
| | Stand. Dev. | 1.6 | | | | | |
| Group 2 CMV-EPO No stimulation | 12 | 45 | ND | ND | ND | 50 | <15 |
| | 13 | 45 | ND | ND | ND | 50 | <15 |
| | 14 | ND | ND | ND | ND | 48 | <15 |
| | 15 | 46 | ND | ND | ND | 49.5 | <15 |
| | 16 | 44 | ND | ND | ND | 52 | <15 |
| | Avg. | 45 | ND | ND | ND | 49.9 | <15 |
| | Stand. Dev. | 0.8 | | | | | |
| Group 3 CMV-GFP Stimulated | 2 | ND | ND | ND | ND | 43.5 | <15 |
| | 3 | ND | ND | ND | ND | 48 | <15 |
| | 5 | ND | ND | ND | ND | 48 | <15 |
| | 6 | ND | ND | ND | ND | 48 | <15 |
| | Avg. | ND | ND | ND | ND | 45.9 | <15 |
| | Stand. Dev. | | | | | 1.8 | <15 |
| Group 4 CMV-EPO | 17 | 45 | ND | ND | <15 | 45.5 | ND |
| | 18 | 45 | ND | ND | <15 | 49 | ND |
| | 19 | 43 | ND | ND | <15 | 48 | ND |
| | 20 | 45 | ND | ND | <15 | 51.5 | ND |
| | 21 | 50 | ND | ND | <15 | 47 | ND |
| | Avg. | 45.6 | ND | ND | <15 | 48.2 | ND |
| | Stand. Dev. | 2.6 | | | | 2.3 | |

ND = not determined.
[a] p < 0.0001 vs. group 2;
[b] p < 0.0001 vs. group 3;
[c] p < 0.0001 vs. group 4; (Fisher's protected least significant difference).

Example 13

Delivery of Non-nucleic Acid Molecules

Figure 20:
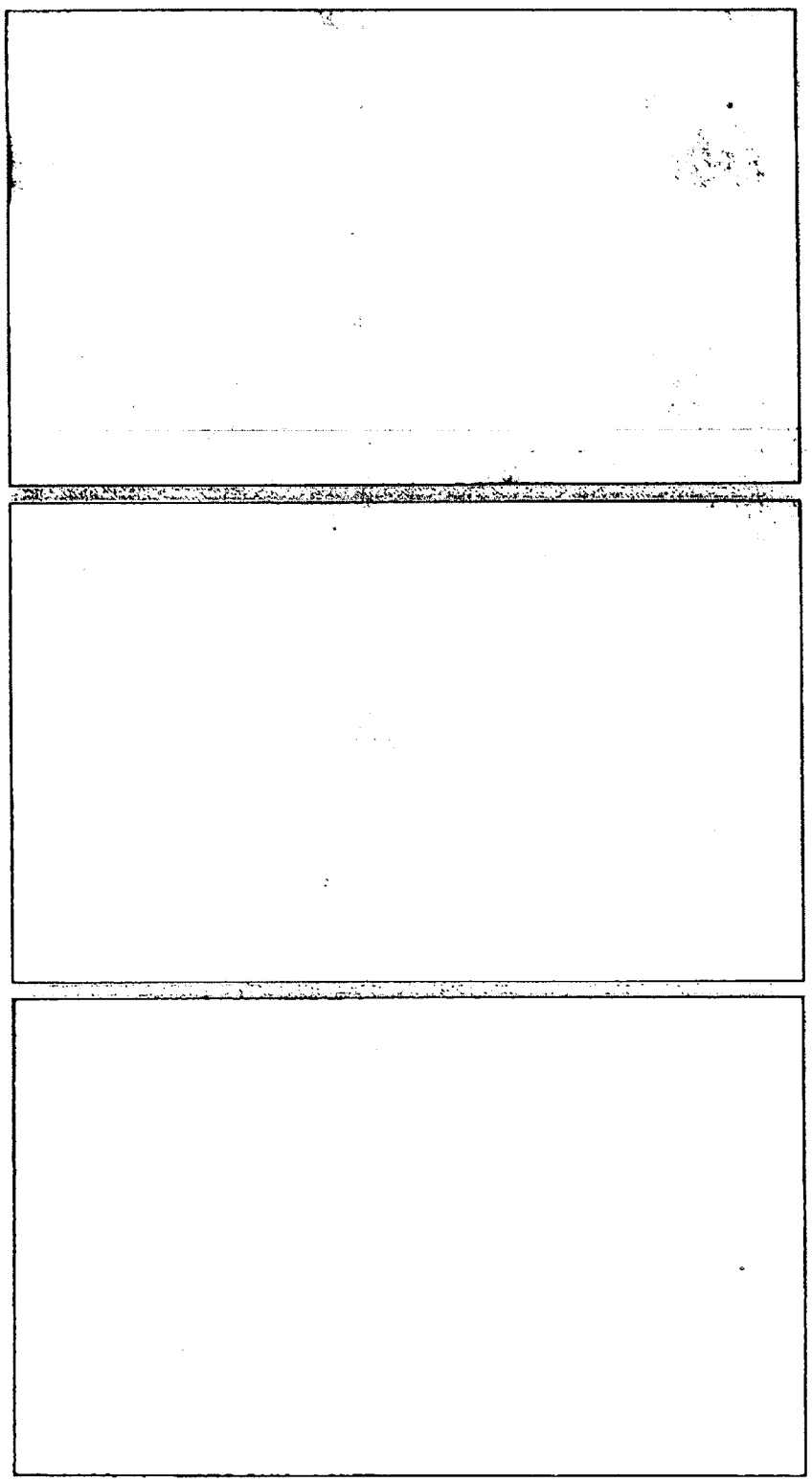
FIG. 20—is a photograph of muscles transfected with rhodamine-conjugated dextran and green fluorescent protein. Top: rhodamin fluorescence from rhodamine conjugated dextran. Middle: The same section as above but with filters revealing GFP fluorescence. Bottom: hematoxilin and eosin staining of a neighboring section.

Muscles were injected with 50 µl of a mixture of GPF plasmid DNA 1 µg/µl and 2 µg/µl rhodamin-conjugated dextran (10 kD from Molecular Probes). Three to 5 days later the muscles (n=6) were frozen in liquid nitrogen and sectioned on a cryostat. As illustrated in FIG. 20, stimulated muscles (bottom) were transfected with rhodamin-conjugated dextran (top) and GFP (middle). As further illustrated, the same muscle fibers were transfected with both GFP and rhodamin-conjugated dextran. These data indicate that non-nucleic acid molecules can be delivered to muscle cells using the technique of the present invention.

Example 14

Materials and Methods for Genetic Immunization

The materials and methods listed below were employed throughout the Examples that follow, i.e., Examples 15–24, except as otherwise indicated.

Protein Purification. Both of the mycobacteria secreted proteins MPB70 and 85B were isolated and purified from culture fluid of *Mycobacterium bovis* BCG Tokyo and BCG Chopenhagen respectively, growing on Sauton media. PBS pH 7.4 was used to resuspend freeze-dried aliquots of the purified proteins to appropriate concentration for immunization or ELISA plate coating.

Plasmids. The following antigen-expressing plasmids were used in these experiments: CMV70 which is the *M bovis* MPB70 protein encoding sequence inserted into the pcDNA3, a mammalian expression vector from Invitrogen (Carlsbad, Calif.) with a CMV promoter (from Hewinson et. al., Central Veterinary Laboratory, Surry, UK).

85b, which contains the *mycobacterium tuberculosis* gene encoding 85B without the mycobacterial signal sequence inserted into the v1Jns-tPA vector from Merck. In this plasmid, the bacterial gene is preceded by the promoter intron A of the first immediate early antigen IEI of CMV (85b from K. Huygen, Pasteur Institute of Brussels, Belgium).

Likewise, 85a is expresses the *mycobacterium tuberculosis* gene encoding the 85A protein, and a different form of 85b that it is inserted into the VR1020 vector from VICAL (from K. Huygen, Pasteur Institute of Brussels, Belgium).

Plasmids from transfected *E. Coli* cultures were amplified and purified by using Genomed Jetstar purification kit, and by Aldevron DNA Purification Service to GMP standards. The purity of our DNA constructs were confirmed by enzyme digestion and agarose-EtBr electrophoresis. The concentration was measured by the 280/260 nm absorption ratio. The stock solution was stored at −20° C. until needed.

The luciferase reporter gene used in these experiments contained a CMV promoter (VR-1255 from VICAL).

Luciferase assay. The assay was performed using the kit developed by Promega, with the organs in question homogenized and added to the assay buffer and purified by centrifugation. Activity was with a TD-20/20, Luminometer from Turner Designs (Sunnyvale, Calif., USA).

Animal experiments. Six- to eight-week-old female B6D2 mice or BalbC mice were anesthetized and used in accordance with Nonvegian rules for animal experiments.

Protein immunization. Mice were immunized subcutaneously with 100 μl equal amount of proteins (MPB70 or 85B) at a concentration of 1 mg/ml in PBS sonicated with Incomplete Freunds Adjuvant (Behringwerke AG, Marburg, Germany).

BCG vaccination/immunization. *Mycobacterium bovis* BCG (Moreau) was harvested from cultures grown in Satoun medium and washed twice with PBS buffer. The spun-down bacteria were homogenized carefully with PBS to an approximate concentration of 200 mg/ml. 100 μl of this suspension was injected subcutaneously into the mice.

DNA injections and immunization with electrical stimulation (EP). Intramuscular injections were given with a 28-gauge insulin needle to deliver 0.5–50 μg of plasmid DNA in 50 μl of physiological saline to quadriceps in mice bilaterally (final concentration of DNA was 0.01, 0.1, or 1 μg/μl, for a total of 1, 10 or 100 μg DNA per mouse). Following the DNA injection, electrodes were placed on the skin to deliver an electric field at the site of DNA delivery. The electroporation was given as 8 trains of 1000 pulses delivered at a frequency of 1000 Hz. Each pulse lasted for 200 μs positive and 200 μs negative for a total pulse duration of total 400 μs. The electrical field strength varied with the change in resistance in the tissue of each animal, but the field strength was in the range of approximately 25–35 V over approximately 2.5–3 mm, or from about 83 V/cm to about 140 V/cm. Each train was delivered at two second intervals, with each train lasting one second.

Serum sampling. Venous blood was taken from the mice after four and eight weeks. Samples were left over night at 4° C. spun down and stored aliquoted at −20° C.

ELISA. ELISA were performed in Costar high-bind microtiter plates coated with native protein (85B or MPB70) 100 p.1 per well, 5 μ/μl in PBS with sodium azide (stable for months). Plates were stored at least over night at 4° C. before use. Before use and between every step, the plates were washed 3 times with PBS+0.1% Tween 20. All incubations were performed at 37° C. for one hour, except the last developing step, which was performed at room temperature for 10 minutes. The assay steps were as follows:

First, blocking was with PBS (without azide) containing 0.5% BSA, followed by application of serum samples diluted 27 or 64 times in PBS dilution buffer (0.2% BSA and 0.2% Tween 20. Biotinylated subtype-specific antibodies (anti-mouse IgG 1 (clone A85-1), anti-mouse IgG2a (R19-15), both Lou Rat IgG1, and IgG2b (R12-3) rat IgG2a) (all three from Pharmingen) were added in a concentration of 0.5μ/ml diluted in PBS dilution buffer. Streptavidin-HRP from Amersham diluted 1:1000 in PBS dilution buffer was then added. The amount of subtype-specific antibodies in serum were measured by OD at 405 nm after adding ABTS substrate in 0.1 M acetate buffer pH 4.0 with 3% $H_2O_2$.

Normalization of OD values in subtype ELISA. A positive control standard included in each ELISA microtiterplate was set to 1.0 (divided by itself). All other values obtained were divided by the positive control value, to be able to compare OD values from different microtiter plates within the same and different experiments.

Example 15

Genetic Immunization with DNA Encoding Mycobacterial Antigens

B6D2 mice were selected for the experiment and divided into three groups. One group received DNA plasmid and electrical stimulation (EP). The second group received only DNA. The third group consisted of control animals, which received only saline and electrical stimulation.

Figure 21A:
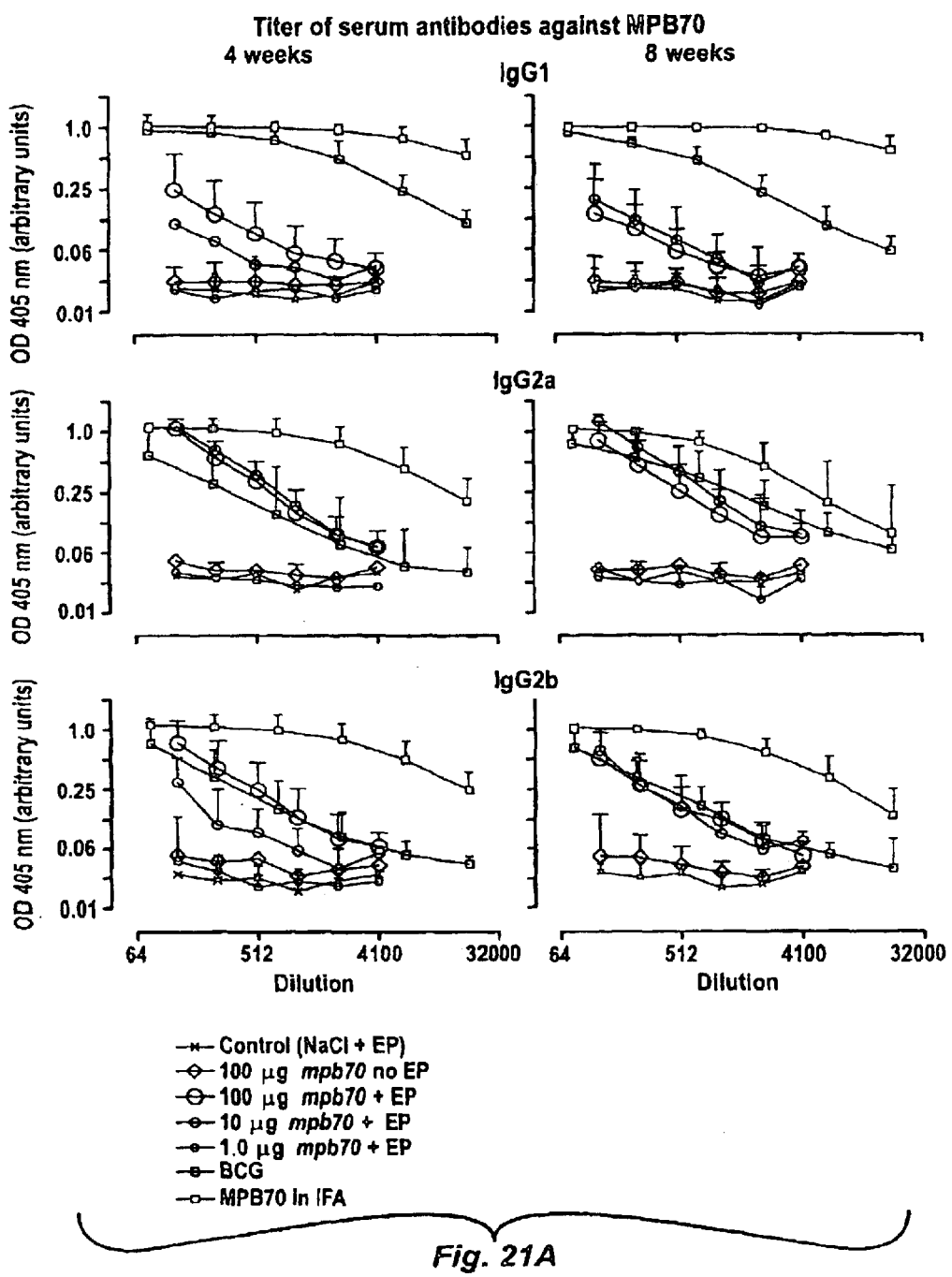
FIG. 21—are graphs illustrating relative amounts of specific subtypes of antibody reactive with given antigens at four and eight weeks after immunization.
Figure 21B:
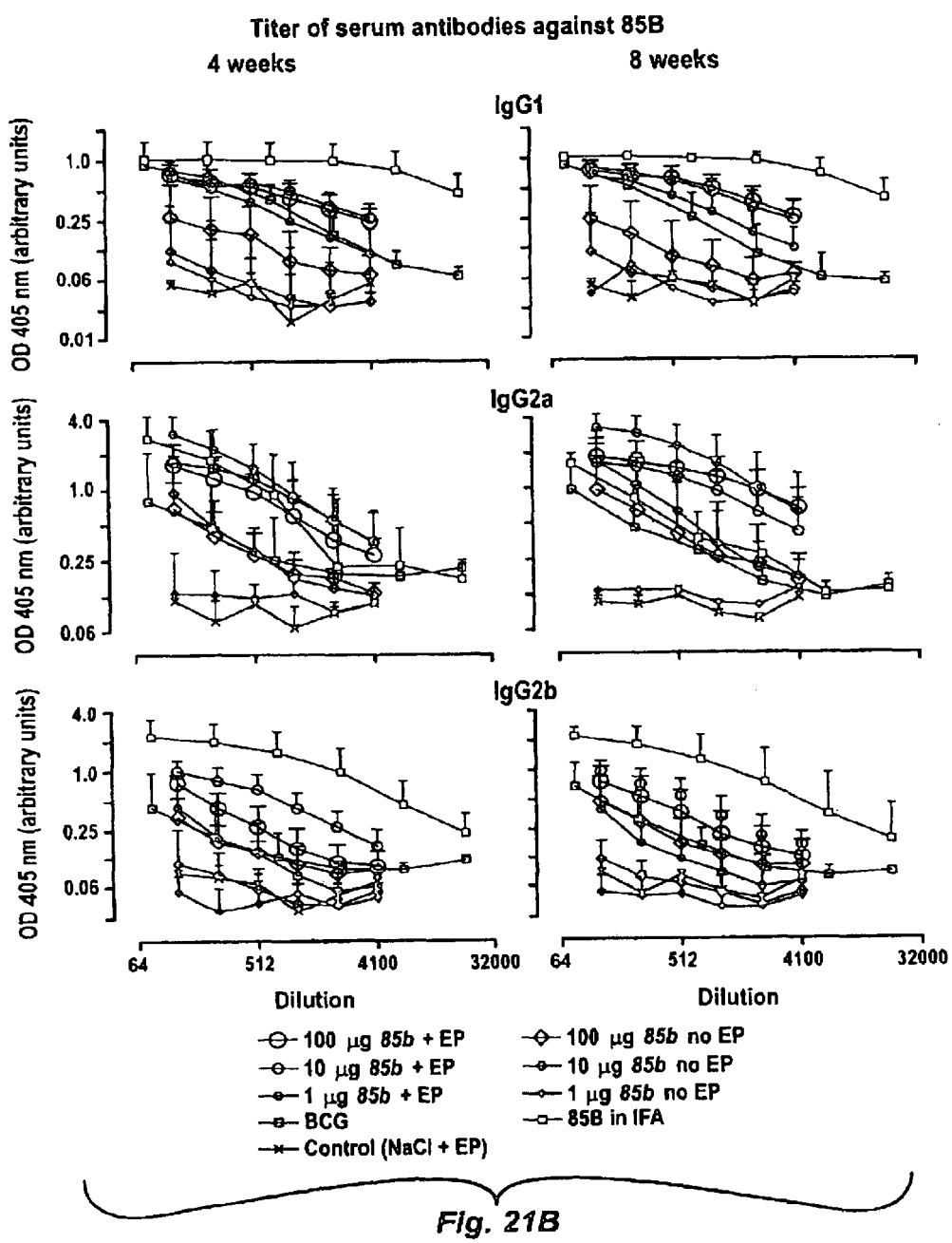

Each of the groups that received DNA were divided into subgroups according of the dose and type of DNA injected. The total DNA dose used in the mice was either 100, 10 or 1.0 μg in 100 μl saline (50 μl in each muscle). In FIG. 21, the symbols refer to different doses of DNA, with each symbol representing the mean titer from a group of mice (5–7 animals). Large symbols represent antibody titer from animals receiving 100 μg DNA; medium-size symbols, 10 μg DNA; and small symbols, 1 μg DNA. Circles represents EP-treated animals and diamonds no EP. Filled squares are from animals immunized with protein in IFA and plain lines (no symbols) are from animals immunized with BCG bacila. Serum samples were tested by an ELISA assay designed for subtyping of antigen (MPB70 or 85B) specific immunoglobulins. The average antibody titer is shown for each group of animals as a function of optical density at 405 nm with serial dilution of serum samples collected at 4 and 8 weeks. The overall pattern is that EP-treated animals react with a significantly higher titer of immunoglobulins to the antigen encoded by the injected plasmid for the three subclasses of immunoglobulin tested.

In mouse, a Th1 cellular immune response is indicated by elevated serum concentration of antigen-specific immunoglobulins of subclass 2a. A humoral Th2 immune response is characterized by increasing antigen-specific IgGI and IgG2b antibodies in serum. Serum samples from DNA-EP immunized mice contained elevated levels of IgG1, IgG2a and IgG2b (FIG. 21). This indicates that the animals react with both humoral and cellular immune responses. Compared with mice that have been immunized with *M. bovis* BCG or protein-IFA, our mice seem to have lower titers of IgGi and IgG2b, but at the same or higher level with regard to IgG2a. These data indicate a strong Th1-associated cellular immune response when the animals are injected with DNA and EP-treated.

The *M. tuberculosis*-specific secreted membrane protein MPB70 tends to elicit a weaker immune response than the widely cross-reacting common mycobacterial antigen 85B. For 85b DNA, all three doses of plasmid with EP give a high immunoglobulin response for the three antibody subclasses tested. However, for mpb70 DNA, only the two highest doses of plasmid injected give a high immunoglobulin response. When the animals were injected with 1 μg of mpb70 DNA, we detected no immune response. Animals that receive more than 1 μg 85b have almost the same antibody titer as an animal that were given 100 μg. For mpb70, the response required a greater dose of DNA.

These results show that the dose of DNA injected into the animals can be reduced at least 100-fold and still give the same or higher immunoglobulin response against the antigen encoded. Without EP, none of the mpb70 animals react against the antigen, but for 85b, the two highest doses of DNA give an immune response, although it is significantly lower than the response in EP-treated animals. This might be because 85B is a common antigen, and the mice might have previously been exposed to it.

We have also studied the gene transfection efficiency by staining for the encoded antigen in frozen cross sections of the quadriceps muscle five days after plasmid DNA injection. By counting positive fibers in a defined area of the muscle section from EP-treated and non-treated animals, we found a nearly hundred-fold increase in antigen expression after EP (data not shown).

Muscle cells normally do not express either MHC class I or II at a detectable level. We have stained for both MHC I and II (mouse anti MHC class I from Pharmingen clone 34-2-12S, mouse anti MHC class II clone 25-29-17, both were directly conjugated with FITC) in frozen sections from the DNA-injected animals. With regard to MHC class I, we find that neither muscle cells nor other cells in the area express MHC I after injection of saline followed by EP. With injection only of plasmid (no EP), the cells in muscle fasciae start to express MHC I at a detectable level. When the animals are injected with plasmid DNA followed by EP treatment, we see enhanced expression of MHC I in both the fasciae and on muscle fibers in the area where there are plasmid-transfected and gene-expressing fibers. Characteristic staining was found, with positive MHC I circular staining in the periphery of transfected fibers and their neighboring fibers, which is seen only in the plasmid transfected area.

MHC class II was detected in the fasciae and in-between muscle fibers only after plasmid injection followed by EP. HAS-staining shows that mononucleated cells are recruited to the area after DNA injection and EP treatment. The area in which we find MHC class II positive cells seems to be co-localized to that in which we find mononucleated cells after HAS staining. Without being bound by any particular theory, this co-localization may result from a combination of two factors. First, EP may cause local damage to the muscle. Second, the expression of a foreign antigen encoded by the injected plasmid function as a strong signal for recruitment of immune cells.

Example 16

Transfection of Immune Cells Residing in Skeletal Muscle of Rats

Three rats were intramuscularly injected in the soleus muscle, surgically exposed, with 25 $\mu$g Luc cDNA dissolved in 50 $\mu$l of 150 mM sodium phosphate buffer pH 7.2. Following the injection, electrodes were inserted into the muscle near the site-of the injection in two of the rats, and electroporation given. The third rat received no electrical stimulation.

After two days, the spleens of the three rats were removed and analyzed for luciferace activity. As shown in Table 5, the luciferace activity in the spleens of the rats that received electrical stimulation was more than ten times greater than the activity the spleen of a rat that did not receive electrical stimulation. These results indicate that transfection of immune cells residing in muscle is increased by electroporation.

TABLE 5

| Spleen | Luc activity | Fold increase after EP |
|---|---|---|
| EP1 | 82 | >10 |
| EP2 | 83 | >10 |
| No EP | 7.5 | |

Example 17

Transfection of Immune Cells Residing in Skeletal Muscle of Mice

Eleven mice were intramuscularly injected into the quadriceps with 50 $\mu$g of Luc plasmid DNA dissolved in 50 $\mu$l of 150 mM sodium phosphate buffer pH 7.2. In six of the eleven mice, the injection was followed by electroporation.

Figure 22:
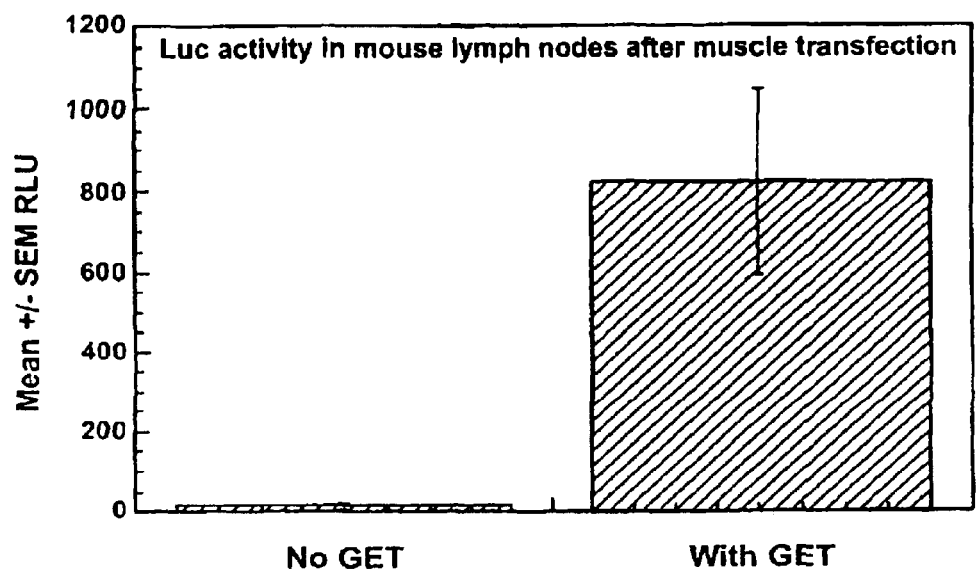
FIG. 22—is a bar graph illustration mean luciferace activity in lymph nodes of mice after transfection of muscle with Luc cDNA.

After two days, the lymph nodes of the mice were removed and analyzed for luciferace activity. As shown in FIG. 22, the luciferace activity in the lymph nodes of the mice that received electroporation exhibited significantly greater luciferace activity that in the mice that did not receive electroporation. These results indicate that electrical stimulation increases the transfection of immune cells residing in the muscle.

Example 18

Transfection of Immune Cells Residing in Skeletal Muscle of Rats

Six rats were intramuscularly injected in both surgically exposed soleus muscles and EDL with 50 $\mu$g of Luc plasmid DNA dissolved in 50 $\mu$l of 150 mM sodium phosphate buffer pH 7.2. After the injection, electrodes were inserted near the injection site and electroporation given to both EDL and Soleus on the right side of the animal.

Figure 23:
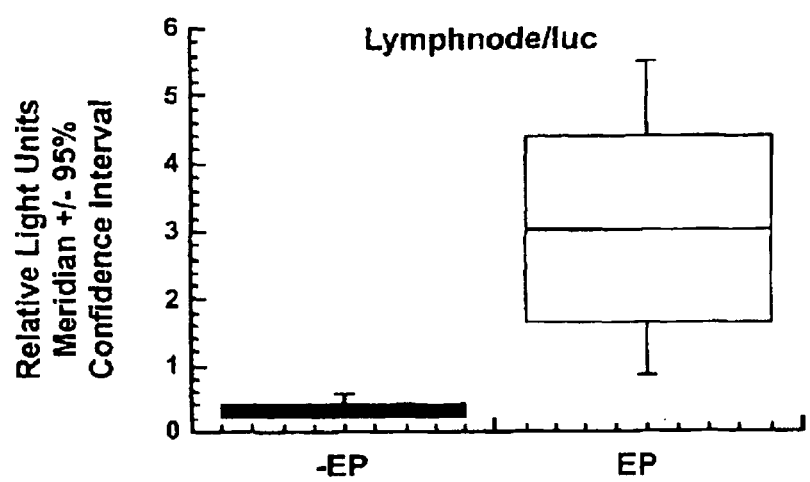
FIG. 23—is a bar graph illustration of mean luciferace activity in lymph nodes of rats after transfection of muscle with Luc cDNA.

After seven days, the lymph nodes of the rats were removed and analyzed for luciferace activity. Referring to FIG. 23, the luciferace activity in the lymph nodes draining the right-side muscles that received electroporation was substantially higher than the activity of the lymph nodes draining the muscles on the left side that did not receive electroporation. These results indicate that electrical stimulation increases the transfection of immune cells residing in the muscle at the time of electroporation. The cells travel to the lymphoid tissue, where they could play a role in inducing an immune response.

Example 19

Use of a Local Anesthetic During Genetic Immunization

Thirty-four mice were separated into groups of five to seven mice. Each mouse was intramuscularly injected in the quadriceps as follows. Group 1, saline+EP; group 2, mpb70 no EP; group 3 mpb70 and EP; group 4 mpb70+marcain but no EP; group 5 mpb70 marcain and EP. Final concentration in the solution containing DNA was I $\mu$g/$\mu$l dissolved in 0.9% NaCl and group 4 & 5 also received 2.5 mg/ml Marcain in the DNA solution. Both muscles in each animal were injected with 50 $\mu$l one of these solutions.

Figure 24:
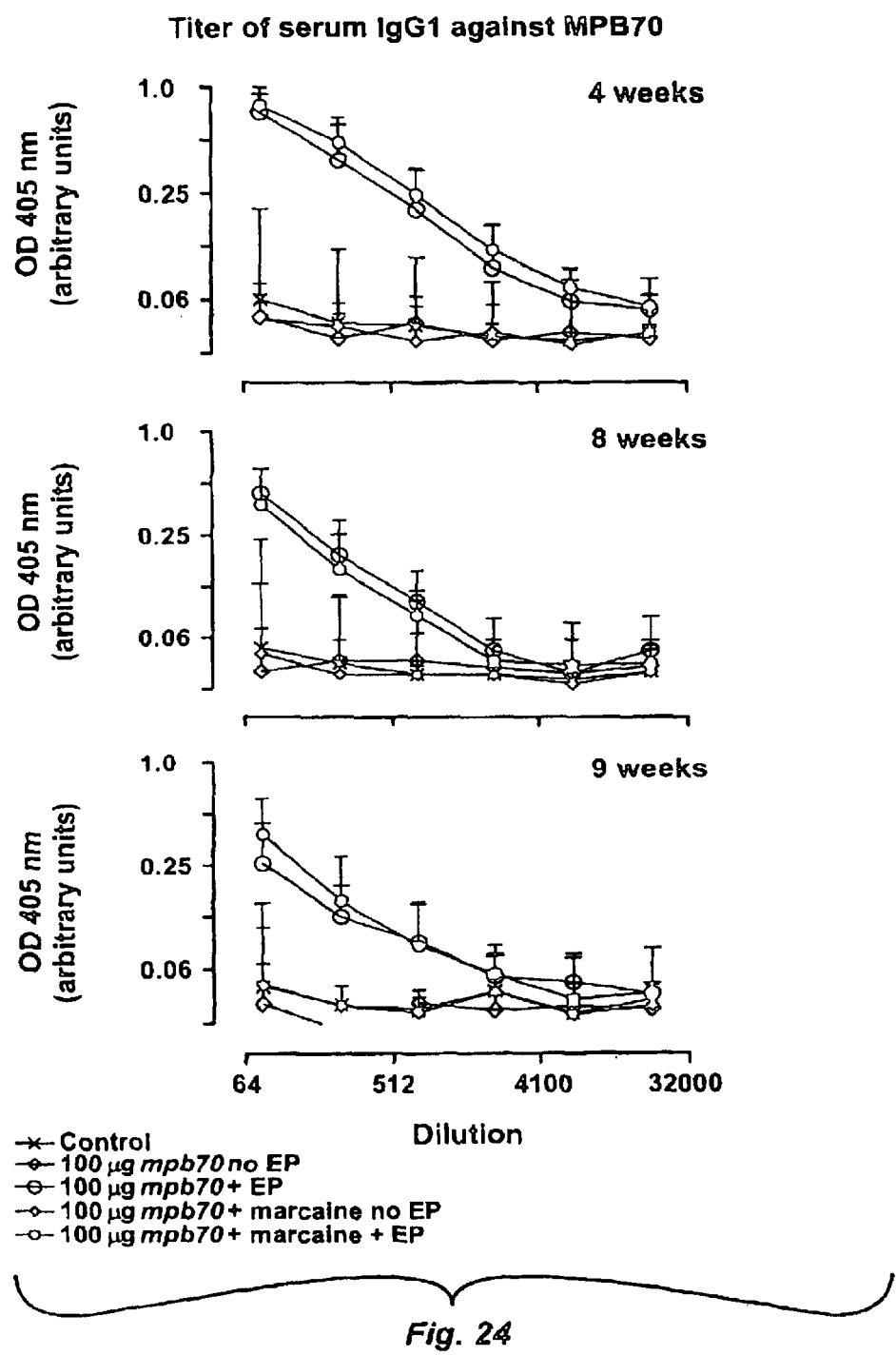
FIG. 24—are graphs illustrating IgG1 antibody levels in mice at 4, 8, and 9 weeks after genetic immunization.
Figure 25:
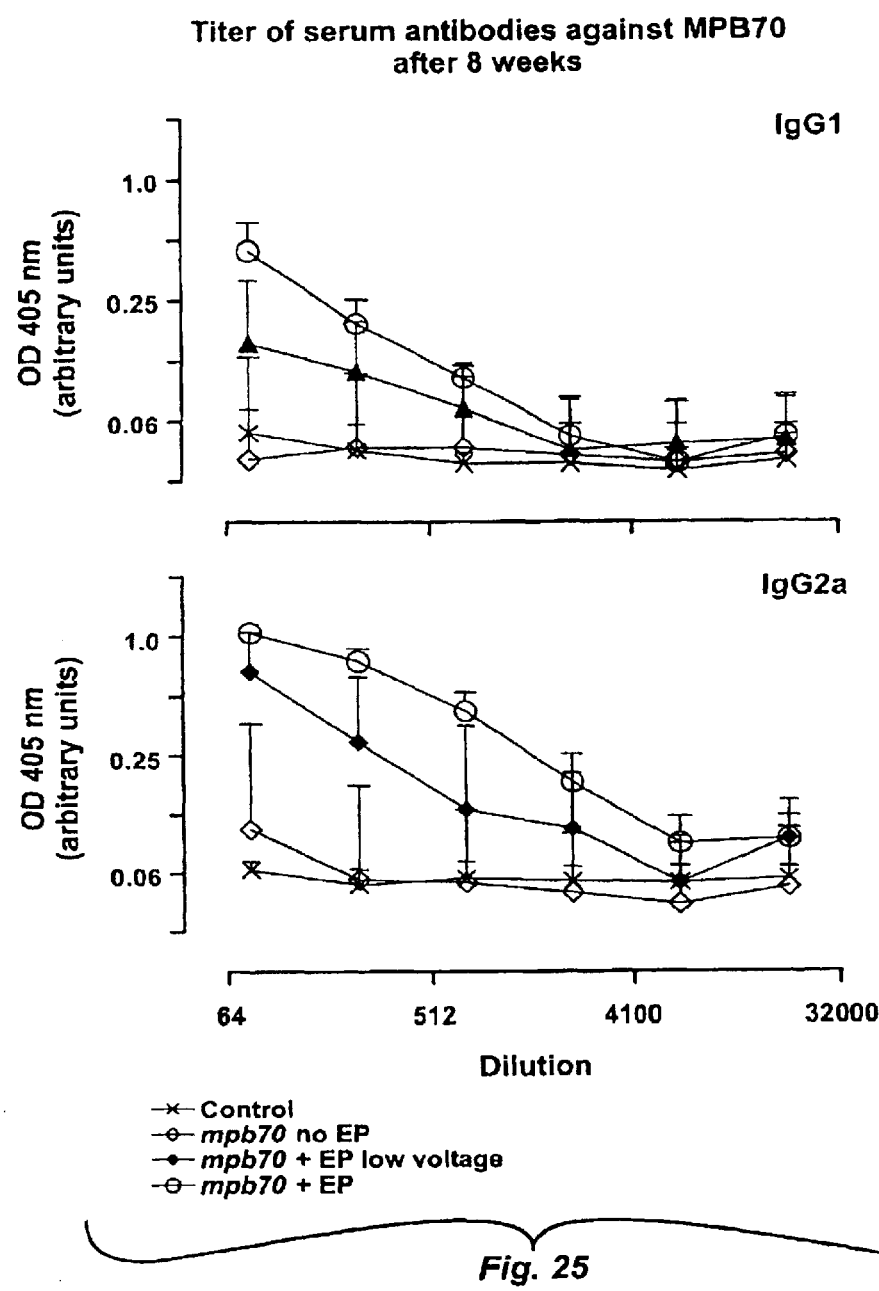
FIG. 25—are graphs illustrating IgG2a antibody levels in mice at 4, 8, and 9 weeks after genetic immunization.
Figure 26:
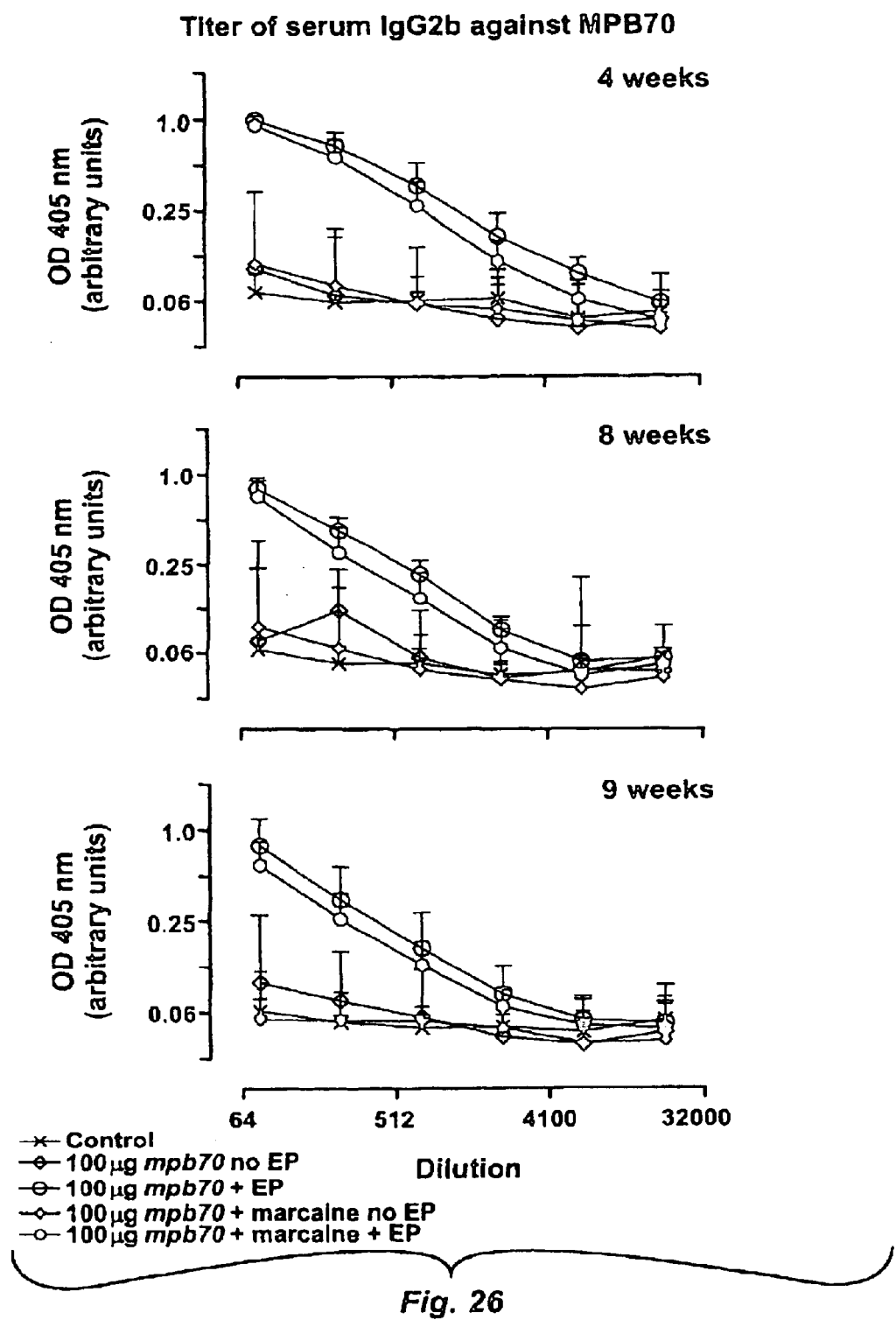
FIG. 26—are graphs illustrating IgG2b antibody levels in mice at 4, 8, and 9 weeks after genetic immunization.

The electrical stimulation was delivered shortly after injection to the muscles of selected mice and given near the site of injection. The sera were collected from the mice at four and eight weeks. A boost injection (50 $\mu$g of mpb70) was given after 8 week. A final ELISA was done on serum collected after 9 weeks. Referring to FIGS. 24 though 26, ELISA analysis of the sera revealed no significant differences between the genetically stimulated immune response in the animals that received Marcain and those that did not. Similar results are obtained with the 85B construct.

Example 20

Use of a Local Anesthetic During Muscle Transfection/Electroporation

Mice were divided into two groups: group I consisted of five mice, group 2 had six mice. Each mouse was injected with 50 $\mu$l with 25 $\mu$g CMV Luc plasmid DNA dissolved in 0.9% NaCl in each left quadriseps muscle. The right muscle received the same amount of DNA but mixed with Marcain to a final concentration of 0.5 $\mu$g/$\mu$l DNA and 2.5 mg/mi Marcain. All muscles in mice in group 1 were not electroporated. All muscles in group 2 received electroporation.

Figure 27:
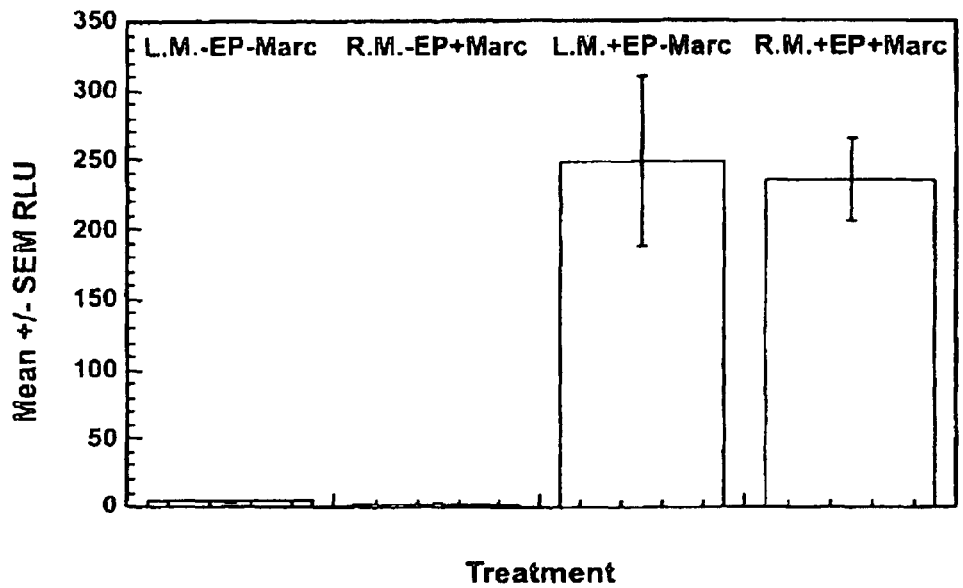
FIG. 27—is a bar graph illustrating luciferace activity in muscle cells 5 days after transfection with Luc plasmid DNA.

After five days, the animals were sacrificed and the quadriceps removed. The muscle were analyzed for luciferace activity. FIG. 27 shows that animals that were injected with either CMV Luc plasmid DNA and or CMV Luc plasmid DNA and Marcain exhibited transfection at a high rate after the electroporation treatment. These data demonstrate that electroporation performed with or without an anaesthetic results in the same level of transfection.

Example 21

Protein Immunization with Electroporation

Six groups of mice were selected for use in the following protocol. Initial immunizations took place on day 0. Each mouse in the first group received an intramuscular injection of a saline solution followed by electroporation. A second group of three mice received an injection of 25 µg 85B protein and electroporation. Another group of three mice were injected with 25 µg 85B protein without electroporation. A group of five mice received 100 µg of 85b DNA in solution without electroporation. Another group of five mice received 10 µg of 85b DNA and electroporation. Finally, a third group of five mice received 100 µg of 85b DNA and electroporation.

Eight weeks after the initial immunization, all animals were given a second immunization in which each animal in all six groups received an intramuscular injection of a mixture of 25 µg of 85b DNA and 1 µg Luc DNA, followed by electroporation. Five days later, the muscles were removed and assayed for luciferace activity. In animals in which a strong cellular immune response was induced by the first immunization, one might expect to see a reduced luciferace activity compared to those animals without a good induction of the cellular immune response. Without being bound by any particular theory, one might expect to see this in two situations: when the cellular immune response is lacking or repressed, or when the humoral branch of the immune system is activated, such that the second immunization with DNA primes the existing humoral response rather than a non-stimulated cellular response.

Figure 28:
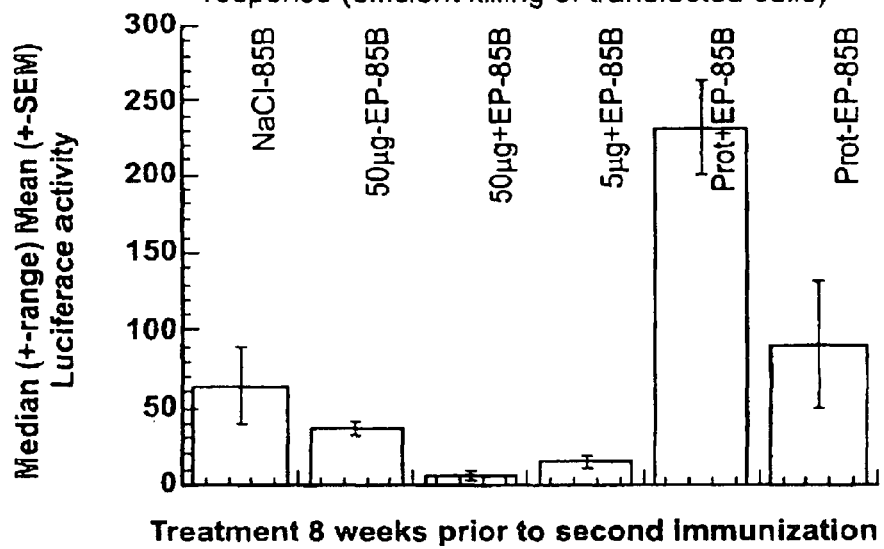
FIG. 28—is a bar graph illustrating mean luciferace activity in mouse muscles after a second immunization with 85B and luciferace cDNA. A low value indicates a strong cellular immune response and efficient killing of transfected cells.

The results of this assay are shown in FIG. 28. The treatment each mouse received on day 0 is written on top of each bar. For example, "NaCl-85B" on top of the bar means the group received saline at day 0 and the mixture of 85b and luciferase at week 8.

DNA without electrical stimulation did not have much effect compared to saline. Both doses of DNA with electrical stimulation had an effect, shown by the low luciferace activity. Without being bound by any particular theory, it appears that transfection at day 0 with electroporation caused a cellular immune response that was rapidly mobilized and killed 85B/Luc-expressing fibers five days after the boost injection at week 8.

However, with the protein, something else occurred as shown by the large increase in luciferace activity. These results could be caused by a type of immune deviation. That is, the immune reaction has changed to a humoral type that was enhanced by the boost injection. This humoral-type immune response did not result in killing of the transfected muscle fibers.

Example 22

Protein Immunization Followed by DNA Booster

Eight mice received NaCl and EP (control group), nine mice received protein 85B (group, 85B+85b), five mice got protein MPB70 (group, MPB70+mpb70) at day 0. The protein was given as an intra muscular injection of 20 vg purified protein 85B or MPB70 and electrical stimulated (right muscle only).

Eight weeks after the initial immunization, the animals were given a booster injection with DNA (35 µg in 50 µl 0.9% NaCl) encoding for the corresponding protein antigen given in the first injection. The control group was split in two: four mice received mpb70 (group NaCl+mpb70) and the other four received 85b group (NaCl+85b). The subsequent antibody response was measured five weeks later with ELISA. If the humoral response was stimulated/primed by the protein injection, one would expect to see a stronger increase in IgG1 antibodies after immunization with DNA.

Figure 29:
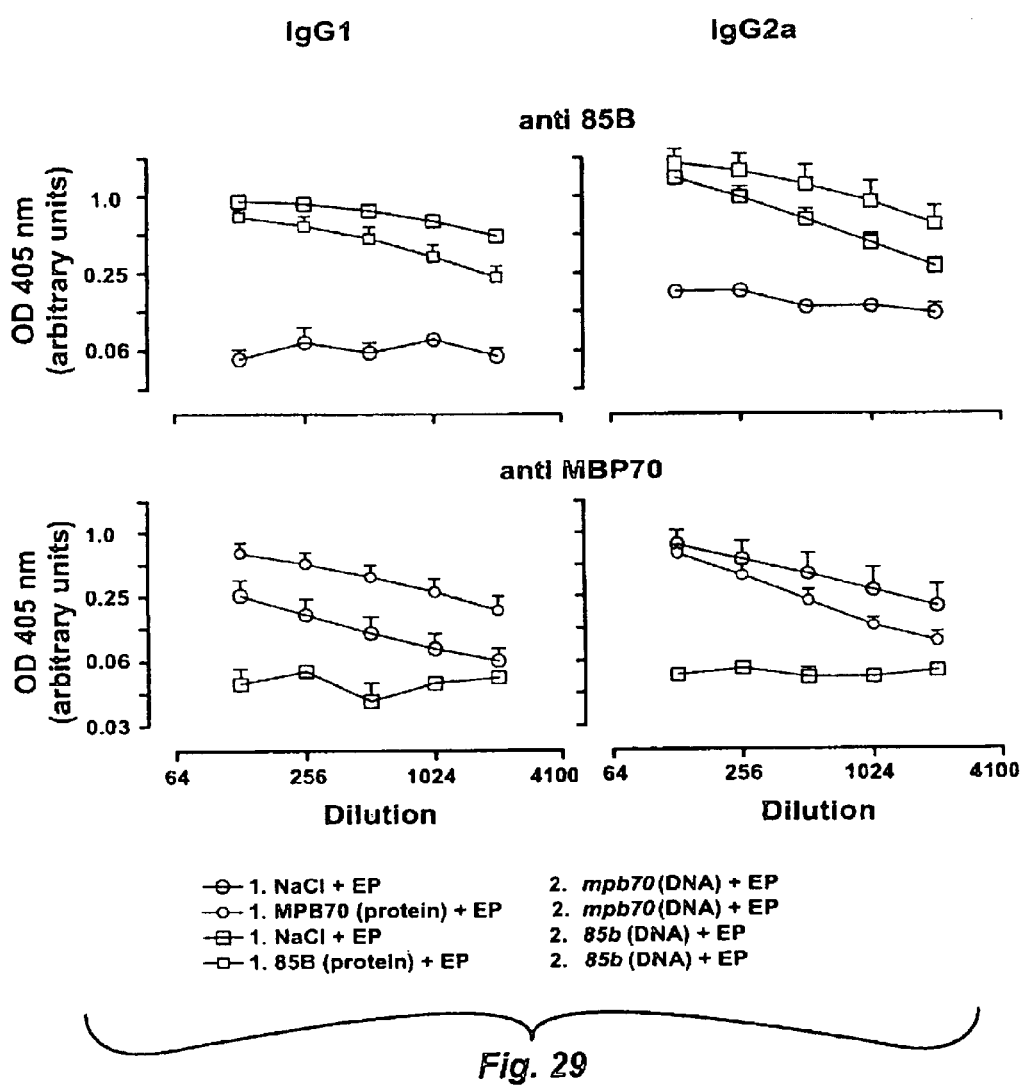
FIG. 29—are graphs illustrating antibody levels after protein immunization. A high level of IgG1 indicates a humoral immune response.

Referring to FIG. 29, an elevated level of IgG1 was detected in the mice that received the initial protein, either 85B or MPB70 vaccination indicating that a humoral response was induced in these mice compared with mice that only received DNA. To demonstrate specificity of the assay, the ELISA was also done on serum from animals immunized with a different construct, hence the 85B ELISA was done on serum from animals that were previously immunized with the mpb70 plasmid (serve as a negative control).

Example 23

Low Voltage DNA Immunization

We have tested relatively low (less than 100 V/cm) electric field strength, which could be used to avoid stimulation of and damage to surrounding tissue. We used a low voltage, which we did not expect would have much effect on transfection of muscle fibers. The low voltage, however, still had a significant effect on immunization.

Four groups of mice were selected for the following protocol. Each mouse was intramuscularly injected in the quadriceps as follows. The first group of six mice were injected with 0.9% saline and exposed to electroporation. Another group of six mice were injected with 100 µg mpb70 plasmid DNA dissolved in 0.9% NaCl and received no electroporation. A third group consisting of seven mice were injected with 100 µg mpb70 plasmid DNA dissolved in 0.9% NaCl and received electroporation at standard field strengths. A final group of seven mice were injected with 100 µg mpb70 plasmid DNA dissolved in 0.9% NaCl and received electroporation at lower field strengths.

The electrical stimulation was delivered shortly after injection and given near the site of injection. Each mouse was electrically stimulated with 8 trains of 1000 pulses at 1000 Hz. Each pulse lasted for 200 µs positive and 200 µs negative for a total pulse duration of total 400 µs. The electrical field strength varied with the change in resistance in the tissue of each animal, but the field strength for the standard voltage level was in the range of approximately 50–70 V over approximately 3–4 mm, or from about 125 to about 233 V/cm. The electric field strength was from about 10 V/cm to about 25 V/cm at the low voltage electroporation. This low voltage stimulation caused strong muscle contraction. Each train was delivered at two second intervals with each train lasting one second.

After four and eight weeks, the sera of the mice was collected and ELISA performed on sera. FIG. 30 shows the results of the eight week ELISA. The results were similar at four weeks, but are not shown. This experiment was also done with a different antigen 85B with similar results.

The eight week results show that low voltage stimulation enhances immune response compared to naked DNA injection. This enhanced immune response could be due to the induced muscle activity or by transfecting cells other than muscle cells such as immune cells residing within the muscle.

Example 24

Increased Numbers of CD8- and CD4-Positive Cells After Immunization Using EP:

Twelve Balb/C mice were separated into four groups. Three mice received 85a and EP, three received 85a without EP, three mice received a plasmid encoding β-galactosidase (β-gal, see previous Examples for details about construct) with EP, and three mice received β-gal without EP. Fourteen days later the spleens were removed from the animals. Cells were isolated and treated according to standard ELISPOT procedures. See Schneider et al, *Nature Medicine* 4:397–402 (1998). Briefly, 1, 0.5 and 0.25 million spleenocytes from each animal were placed in duplicates of antibody-coated wells (anti-mouse INF-gamma mAb R4-6A2, hybridoma from European Collection of Animal Cell Cultures). Peptides (concentration 1 µg/ml) were added to each test well. Control wells received irrelevant peptide. After incubation overnight, plates were washed and incubated for 3 hours with a solution of 1 µg/ml biotinylated anti-mouse INF-gamma mAb XMGI.2 (Pharmingen, Calif.), washed, and incubated for 2 hr with 50 µl of a 1 mg/ml solution of Streptavidin-Alkaline-Phosphatase polymer (Sigma) at RT. Spots were developed by adding 50 µl of an alkaline phosphatese conjugated substrate solution (Biorad, Hercules, Calif.) and reactions were stopped by washing with water. Spots were counted electronically.

The peptides used to stimulate spleenocytes from 85a immunized animals were: P-11, an epitope from 85A that specifically binds to MHC class I and thereby stimulates CD8 positive cells (FIG. 31A); P-15, an epitope from 85A that specifically binds to MHC class H and thereby stimulates CD4 positive cells (FIG. 31B). See Denis et al., *Infect. Immun.* 66:1527–1533 (1998) for details about the peptides.

The peptide used to stimulate spleenocytes from β-Gal immunized animals were AA-876-884 from *E. Coli* beta-galactosidase, this peptide specifically binds to MHC class I and thereby stimulates CD8-positive cells. See FIG. 31C.

Figure 31:
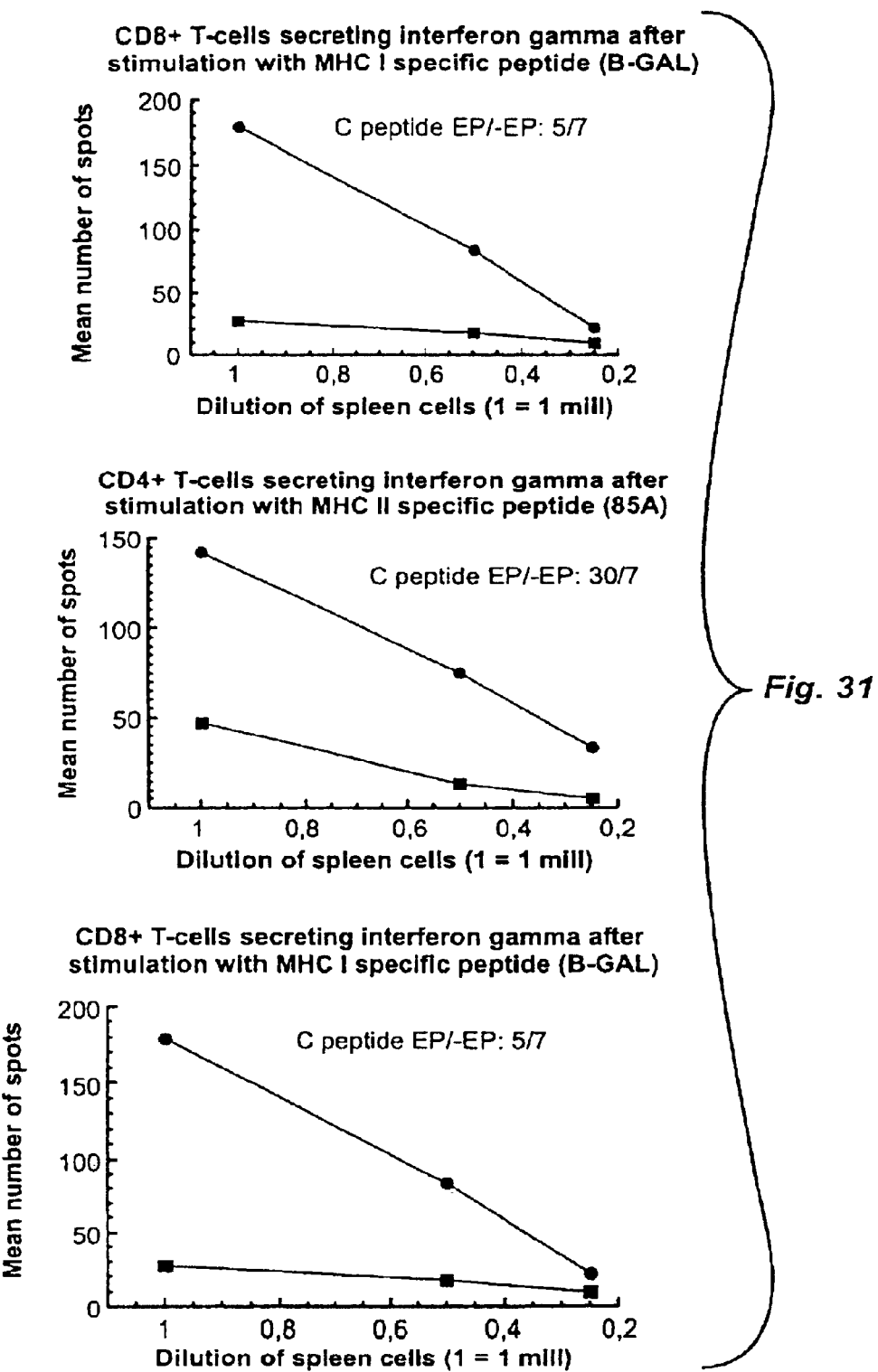
FIG. 31—are graphs illustrating the responses of T-cells from immunized animals to the indicated peptides.

Results shown in FIG. 31 demonstrate an increased number of both CD4 and CD8 positive T-cells when immunization is done in combination with EP. Hence, the cellular branch of the immune system is stimulated.

A high number of CD8- and CD4-positive T-cells is often associated with good protection against many serious infectious diseases in vaccinated humans. It is also believed to be important in protection and the treatment of cancer.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method of delivering a molecule to the skeletal muscle of a mammal in vivo, comprising:
   (a) injecting a molecule into skeletal muscle of a mammal, whereby a penetration site and a treatment region are created;
   (b) positioning electrodes spaced from said penetration site such that current traveling between the electrodes passes through the treatment region; and
   (c) electrically stimulating the muscle with an electrical current.

2. The method of claim 1, wherein said current generates a field strength in the range of from about 25 V/cm to less than 250 V/cm.

3. The method of claim 1, wherein said electrical stimulation is delivered in the form of a single pulse.

4. The method of claim 3, wherein said pulse has a duration of between about 50 µs and 5000 µs.

5. The method of claim 1, wherein said electrical stimulation is delivered in the form of between about 2 to 30,000 pulses.

6. The method claim 5, wherein said pulses have a total duration of between about 10 ms to 12,000 ms.

7. The method of claim 6, wherein said pulses are delivered in the form of at least two trains.

8. The method of claim 7, wherein the frequency of said electrical stimulation is between about 0.5 Hz and 1000 Hz.

9. The method of claim 1, wherein said molecule is a nucleic acid.

10. The method of claim 9, wherein said nucleic acid encodes a protein and said encoded protein is expressed by muscle cells following step c.

11. A method of delivering a molecule to the skeletal muscle of a mammal in vivo, comprising:
    (a) injecting a molecule into skeletal muscle of a mammal, whereby a penetration site and a treatment region are created;
    (b) positioning electrodes spaced from said penetration site such that current traveling between the electrodes passes through the treatment region; and
    (c) electrically stimulating the muscle with a fixed electrical current that results in field strength that varies with tissue resistance, said field strength varying from about 25 V/cm to less than about 250 V/cm.

12. The method of claim 11, wherein said electrical stimulation is delivered in the form of a single pulse.

13. The method of claim 12, wherein said pulse has a duration of between about 50 µs and 5000 µs.

14. The method of claim 11, wherein said electrical stimulation is delivered in the form of between about 2 to 30,000 pulses.

15. The method of claim 14, wherein said pulses have a total duration of between about 10 ms to 12,000 ms.

16. The method of claim 15, wherein said pulses are delivered in the form of at least two trains.

17. The method of claim 16, wherein the frequency of said electrical stimulation is between about 0.5 Hz and 1000 Hz.

18. The method of claim 11, wherein said molecule is a nucleic acid.

19. The method of claim 18, wherein said nucleic acid encodes a protein and said encoded protein is expressed by muscle cells following step c.

20. A method of expressing a polypeptide in a mammal, comprising:
    (a) injecting one or more expression vectors into skeletal muscle of a mammal, whereby a penetration site and a treatment region are created, wherein (i) said vector contains a nucleic acid segment that encodes a polypeptide and (ii) said segment is under genetic control suitable to express said polypeptide in cells of said mammal;
    (b) positioning electrodes spaced from said penetration site such that current traveling between the electrodes passes through the treatment region; and;
    (c) electrically stimulating the muscle with an electrical current.

21. The method of claim 20, wherein said current generates a field strength in the range of from about 25 V/cm to less than 250 V/cm.

22. The method of claim 20, wherein said electrical stimulation is delivered in the form of a single pulse.

23. The method of claim 22, wherein said pulse has a duration of between about 50 $\mu$s and 5000 $\mu$s.

24. The method of claim 20, wherein said electrical stimulation is delivered in the form of between about 2 to 30,000 pulses.

25. The method of claim 24, wherein said pulses have a total duration of between about 10 ms to 12,000 ms.

26. The method of claim 25, wherein said pulses are delivered in the form of at least two trains.

27. The method of claim 26, wherein the frequency of said electrical stimulation is between about 0.5 Hz and 1000 Hz.

28. A method of expressing a polypeptide in a mammal, comprising:

(a) injecting one or more expression vectors into skeletal muscle of a mammal, whereby a penetration site and a treatment region are created, wherein (i) said vector contains a nucleic acid segment that encodes a polypeptide and (ii) said segment is under genetic control suitable to express said polypeptide in cells of said mammal;

(b) positioning electrodes spaced from said penetration site such that current traveling between the electrodes passes through the treatment region; and (c) electrically stimulating the muscle with an a fixed electrical current that results in field strength that varies with tissue resistance, said field strength varying from about 25 V/cm to less than about 250 V/cm.

29. The method of claim 28, wherein said electrical stimulation is delivered in the form of a single pulse.

30. The method of claim 29, wherein said pulse has a duration of between about 50 $\mu$s and 5000 $\mu$s.

31. The method of claim 28 wherein said electrical stimulation is delivered in the form of between about 2 to 30,000 pulses.

32. The method of claim 31 wherein said pulses have a total duration of between about 10 ms to 12,000 ms.

33. The method of claim 32, wherein said pulses are delivered in the form of at least two trains.

34. The method of claim 33, wherein the frequency of said electrical stimulation is between about 0.5 Hz and 1000 Hz.

* * * * *